(12) United States Patent
Melius et al.

(10) Patent No.: US 6,323,388 B1
(45) Date of Patent: Nov. 27, 2001

(54) ABSORBENT ARTICLE WITH AN IMPROVED, WET-FORMED ABSORBENT

(75) Inventors: Shannon Kathleen Melius, Appleton; David Arthur Fell, Neenah; Violet May Grube, Greenville; Andrew Edsel Huntoon, Appleton; Toan Thanh LeMinh, Greenville; Sridhar Ranganathan; William Grover Reeves, both of Appleton; Lawrence Howell Sawyer; Dave Allen Soerens, both of Neenah; Heather Anne Sorebo, Appleton; Michael William Veith, Oshkosh; Palani Raj Ramaswami Wallajapet, Wauwatosa; David Louis Zenker, Neenah, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/334,152

(22) Filed: Jun. 16, 1999

Related U.S. Application Data

(60) Provisional application No. 60/107,068, filed on Nov. 4, 1998.

(51) Int. Cl.[7] .................................................... A61F 13/15
(52) U.S. Cl. ...................... 604/368; 604/385.01; 604/378
(58) Field of Search .......................... 604/385.01, 385.23, 604/367, 368, 378

(56) References Cited

U.S. PATENT DOCUMENTS

| | | | |
|---|---|---|---|
| 3,881,490 | * | 5/1975 | Whitehead et al. . |
| 3,901,236 | * | 8/1975 | Assarsson et al. . |
| 3,902,230 | * | 9/1975 | Schwarz . |
| 4,076,663 | * | 2/1978 | Masuda et al. . |
| 4,117,184 | * | 9/1978 | Erickson et al. . |
| 4,223,059 | * | 9/1980 | Schwarz . |

(List continued on next page.)

FOREIGN PATENT DOCUMENTS

| | | |
|---|---|---|
| 681755 | 7/1995 | (AU) . |
| 0 217 032 A2 | 4/1987 | (EP) . |

(List continued on next page.)

OTHER PUBLICATIONS

Billmeyer, Jr., Fred W., "Textbook of Polymer Science, Third Edition", p. 7.
Buchholz, Fredric L./Graham, Andrew T., Wiley–VCH, "Modern Superabsorbent Polymer Technology", 1998, pp. 45 and 140–143.

(List continued on next page.)

*Primary Examiner*—Dennis Ruhl
(74) *Attorney, Agent, or Firm*—Paul Yee

(57) ABSTRACT

The present invention provides an absorbent article ( 10) having a longitudinal direction ( 26), and a lateral, cross direction ( 24). The article includes a liquid permeable top sheet layer ( 28), a substantially liquid impermeable backsheet layer ( 30), and an absorbent structure ( 32) having a primary retention portion ( 48) sandwiched between the top sheet and backsheet layers. The retention portion ( 48) includes a wet-formed mixture of fibers and superabsorbent material. The retention portion has a selected edge-wise compression value, such as an edge-wise compression value of not more than a maximum of about 9 g/gsm, and a modified circular bend value, such as a modified circular bend value of at least minimum of about 0.3 g/gsm. In particular aspects, the retention portion ( 48) can include cellulosic fibers.

18 Claims, 8 Drawing Sheets

U.S. PATENT DOCUMENTS

| | | | |
|---|---|---|---|
| 4,260,443 | * | 4/1981 | Lindsay et al. . |
| 4,285,100 | * | 8/1981 | Schwarz . |
| 4,286,082 | * | 8/1981 | Tsubakimoto et al. . |
| 4,347,092 | * | 8/1982 | Hlaban et al. . |
| 4,354,901 | * | 10/1982 | Kopolow . |
| 4,500,316 | * | 2/1985 | Damico . |
| 4,552,618 | * | 11/1985 | Kopolow . |
| 4,605,402 | * | 8/1986 | Iskra . |
| 4,610,678 | * | 9/1986 | Weisman et al. . |
| 4,646,362 | * | 3/1987 | Heran et al. . |
| 4,663,220 | * | 5/1987 | Wisneski et al. . |
| 4,685,914 | | 8/1987 | Holtman . |
| 4,699,823 | * | 10/1987 | Kellenberger et al. . |
| 4,701,177 | * | 10/1987 | Ellis et al. . |
| 4,704,116 | * | 11/1987 | Enloe . |
| 4,753,646 | * | 6/1988 | Enloe . |
| 4,851,069 | * | 7/1989 | Packard et al. . |
| 4,886,512 | * | 12/1989 | Damico et al. . |
| 4,916,005 | * | 4/1990 | Lippert et al. . |
| 4,921,543 | * | 5/1990 | Omran et al. . |
| 4,921,643 | * | 5/1990 | Walton et al. . |
| 4,938,753 | * | 7/1990 | Van Gompel et al. . |
| 4,940,464 | | 7/1990 | Van Gompel et al. . |
| 4,986,882 | | 1/1991 | Mackey et al. . |
| 5,019,073 | | 5/1991 | Roessler et al. . |
| 5,049,235 | | 9/1991 | Barcus et al. . |
| 5,102,501 | | 4/1992 | Eber et al. . |
| 5,226,992 | | 7/1993 | Morman . |
| 5,252,275 | | 10/1993 | Sultze et al. . |
| 5,324,575 | | 6/1994 | Sultze et al. . |
| 5,399,219 | | 3/1995 | Roessler et al. . |
| 5,401,267 | | 3/1995 | Couture-Dorschner . |
| 5,411,497 | | 5/1995 | Tanzer et al. . |
| 5,425,725 | | 6/1995 | Tanzer et al. . |
| 5,433,715 | | 7/1995 | Tanzer et al. . |
| 5,486,166 | | 1/1996 | Bishop et al. . |
| 5,490,846 | | 2/1996 | Ellis et al. . |
| 5,509,915 | | 4/1996 | Hanson et al. . |
| 5,540,796 | | 7/1996 | Fries . |
| 5,558,659 | | 9/1996 | Sherrod et al. . |
| 5,562,645 | | 10/1996 | Tanzer et al. . |
| 5,562,650 | | 10/1996 | Everett et al. . |
| 5,593,399 | | 1/1997 | Tanzer et al. . |
| 5,595,618 | | 1/1997 | Fries et al. . |
| 5,601,542 | | 2/1997 | Melius et al. . |
| 5,605,735 | | 2/1997 | Zehner et al. . |
| 5,607,550 | | 3/1997 | Akers . |
| 5,624,429 | | 4/1997 | Long et al. . |
| 5,651,862 | | 7/1997 | Anderson et al. . |
| 5,669,901 | | 9/1997 | LaFortune et al. . |
| 5,820,973 | | 10/1998 | Dodge, II et al. . |
| 5,858,515 | | 1/1999 | Stokes et al. . |
| 5,904,675 | | 5/1999 | Laux et al. . |
| 5,948,829 | * | 12/1999 | Wallajapet et al. ............. 521/64 |
| 5,985,434 | * | 11/1999 | Qin et al. ............. 428/315.5 |
| 6,007,528 | * | 12/1999 | Osborn, III ............. 604/387 |
| B1 4,315,508 | * | 11/1988 | Bolick . |
| B1 5,147,343 | | 3/1998 | Kellenberger . |

FOREIGN PATENT DOCUMENTS

| | | |
|---|---|---|
| 0 359 615 A1 | 3/1990 | (EP) . |
| 0 437 816 B1 | 7/1995 | (EP) . |
| 0 690 077 A1 | 1/1996 | (EP) . |
| WO 93/21879 A1 | 11/1993 | (WO) . |
| WO 96/32084 A1 | 10/1996 | (WO) . |
| WO 98/24392 A1 | 6/1998 | (WO) . |
| WO 98/24621 A1 | 6/1998 | (WO) . |
| WO 98/24960 A1 | 6/1998 | (WO) . |
| WO 98/27276 A1 | 6/1998 | (WO) . |
| WO 98/51251 A1 | 11/1998 | (WO) . |

OTHER PUBLICATIONS

"Acrylic Ester Polymers," *Kirk–Othmer Encyclopedia of Chemical Technology*, Fourth Edition, vol. 1, John Wiley & Sons Publishers, 1991, pp. 315–317.

Fellers, Christer, "Edgewise Compression Strength of Paper," *Handbook of Physical and Mechanical Testing of Paper and Paperboard*, vol. 1, 1983, pp. 349–381.

American Society for Testing Materials (ASTM) Designation: D 4032–82, "Standard Test Method for Stiffness of Fabric by the Circular Bend Procedure," pp. 702–706, published Aug. 1982.

Federal Test Method Standard (FTMS) No. 191A, Method 5514, "Water Resistance of Cloth; Low Range, Hydrostatic Pressure Method," Jul. 20, 1978, 3 pages.

TAPPI Official Test Method T 543 om–94, "Bending Resistance of Paper (Gurley Type Tester)," published by the TAPPI Press, Atlanta, Georgia, pp. 1–7.

* cited by examiner

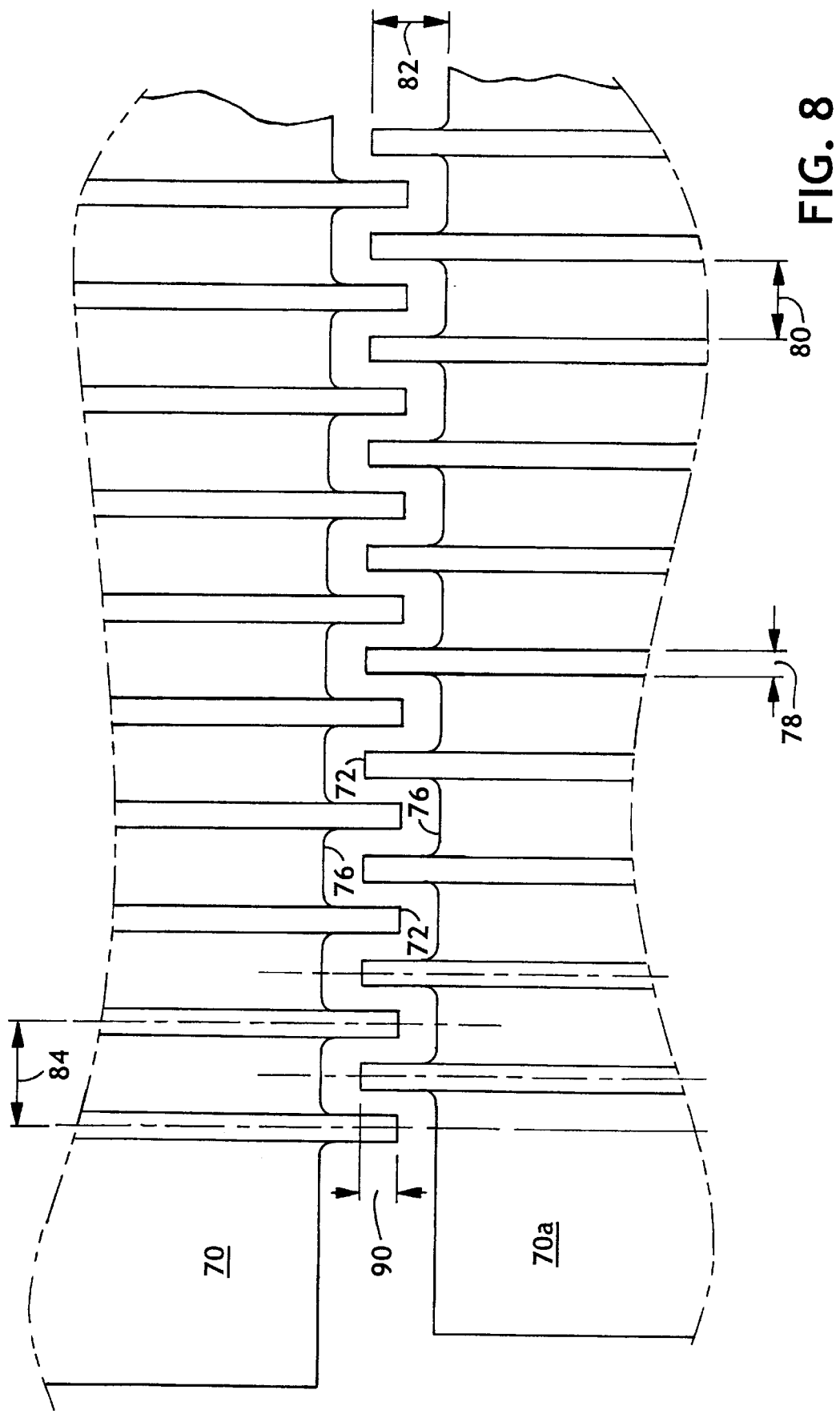

ABSORBENT ARTICLE WITH AN IMPROVED, WET-FORMED ABSORBENT

This application claims priority from presently copending U.S. provisional Application No. 60/107,068 entitled "An Absorbent Article With Improved, Wet-Formed Absorbent" and filed on Nov. 4, 1998, in the name of Shannon Kathleen Melius, David Arthur Fell, Violet May Grube, Andrew Edsel Huntoon, Toan Thanh LeMinh, Sridhar Ranganathan, William Grover Reeves, Lawrence Howell Sawyer, Dave Allen Soerens, Heather Anne Sorebo, Michael William Veith, Palani Raj Ramaswami Wallajapet, and David Louis Zenker.

FIELD OF THE INVENTION

The present invention relates to absorbent articles. More particularly, the present invention relates to absorbent articles which include an absorbent structure formed from a liquid-bearing precursor material and configured with desired structural properties. The absorbent product can incorporate a wet-formed absorbent structure which exhibits desired levels of softness and flexibility when the absorbent structure is dry and when the absorbent structure is wet.

BACKGROUND OF THE INVENTION

The performance objectives of disposable absorbent articles, such as infant diapers, include leakage prevention, dry feel to the wearer, and a comfortable fit throughout the product life. Accordingly, absorbent articles have typically contained an absorbent core to provide liquid handling and other absorbent functionalities required to meet the product performance objectives. The absorbent core of a conventional absorbent article has typically been composed of absorbent fibers, and a superabsorbent material has typically been combined with the absorbent fibers to increase the liquid absorbent capacity. The absorbent core has been formed in a substantially rectangular shape. The absorbent core has also been formed in an hourglass shape, a T-shape, or similar configuration with a reduced absorbent width in the central crotch region for improved fit and comfort.

Conventional absorbent cores have incorporated dry-formed materials which have been produced with various conventional airlaying techniques. The airlaying techniques have typically laid an air-directed mixture of absorbent fibers and superabsorbent to form a web of the absorbent material.

When dry, the conventional dry-formed absorbent structures have been soft and conformable, but have had low strength. In addition, the dry-formed structures have had low integrity after they have been wetted.

As a result, additional components, such as supplemental carrier tissues or supplemental high-strength fibers have been employed to provide sufficient strength to the dry-formed absorbent materials and to provide increased wet integrity. The added dry strength can, for example, allow the dry-formed materials to be more readily passed through conventional manufacturing processes, and the wet integrity can help the absorbent material maintain its shape and structure after the material has absorbed liquid.

Conventional absorbent cores have also incorporated wet-formed materials which have been produced with various wet-laying techniques. The wet-laying techniques have typically formed an absorbent web produced from a precursor material composed of a mixture of fibers and superabsorbent particles combined with water or other aqueous liquid. A particular wet-laying technique has processed the precursor material into a foam, and the foam has then been employed to form the desired web of absorbent material.

The absorbent structures produced from wet-formed absorbent materials have had greater strength and greater integrity. In particular, the wet-formed absorbent structures have exhibited greater strength and greater integrity after the absorbent materials have absorbed liquid. The wet-formed absorbent materials, however, have also had excessive stiffness and rigidity, particularly when the absorbent materials have been provided at the basis weights and amounts needed to provide desired levels of total absorbent capacity.

Consequently, there remains a need for absorbent structures which can provide desired combinations of strength, softness, flexibility, wet integrity and absorbent capacity.

BRIEF DESCRIPTION OF THE INVENTION

Generally stated, the present invention provides an absorbent article having a longitudinal direction, and a lateral, cross direction. The article includes a liquid permeable top sheet layer, a substantially liquid impermeable backsheet layer, and an absorbent structure sandwiched between the top sheet and backsheet layers. The absorbent structure can include a wet-formed mixture of fibers and superabsorbent material, and can have selected properties, such as a selected edge-wise compression value, and a selected modified circular bend value. In particular aspects, the retention portion can include cellulosic fibers.

The present invention provides a distinctive absorbent structure formed from a liquid-containing precursor material which includes a mixture of fibers and superabsorbent particles. The absorbent structure exhibits desirable physical properties, such as softness, flexibility and conformance in both its dry and wet states. When wet, the absorbent structure can advantageously resist separating, bunching and clumping. Since the absorbent structure can better retain its integrity when wet, it can resist becoming mushy and sagging, particularly in the crotch region of the product. As a result, the absorbent structures and articles of the invention can provide increased strength, improved fit, reduced leakage, and reduced clumping, bunching or sagging during use.

BRIEF DESCRIPTION OF THE DRAWINGS

The present invention will be more fully understood and further advantages will become apparent when reference is made to the following detailed description of the invention and the drawings, in which:

FIG. 8 representatively shows an enlarged view of a portion of the softening rollers of FIG. 7.

DETAILED DESCRIPTION OF THE INVENTION

The various aspects and embodiments of the invention will be described in the context of a disposable absorbent article, such as a disposable diaper. It is, however, readily apparent that the present invention could also be employed with other articles, such as gowns, covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Accordingly, such terms are intended to be synonymous with the words "has", "have", "having", "includes", "including" and any derivatives of these words.

Figure 1:
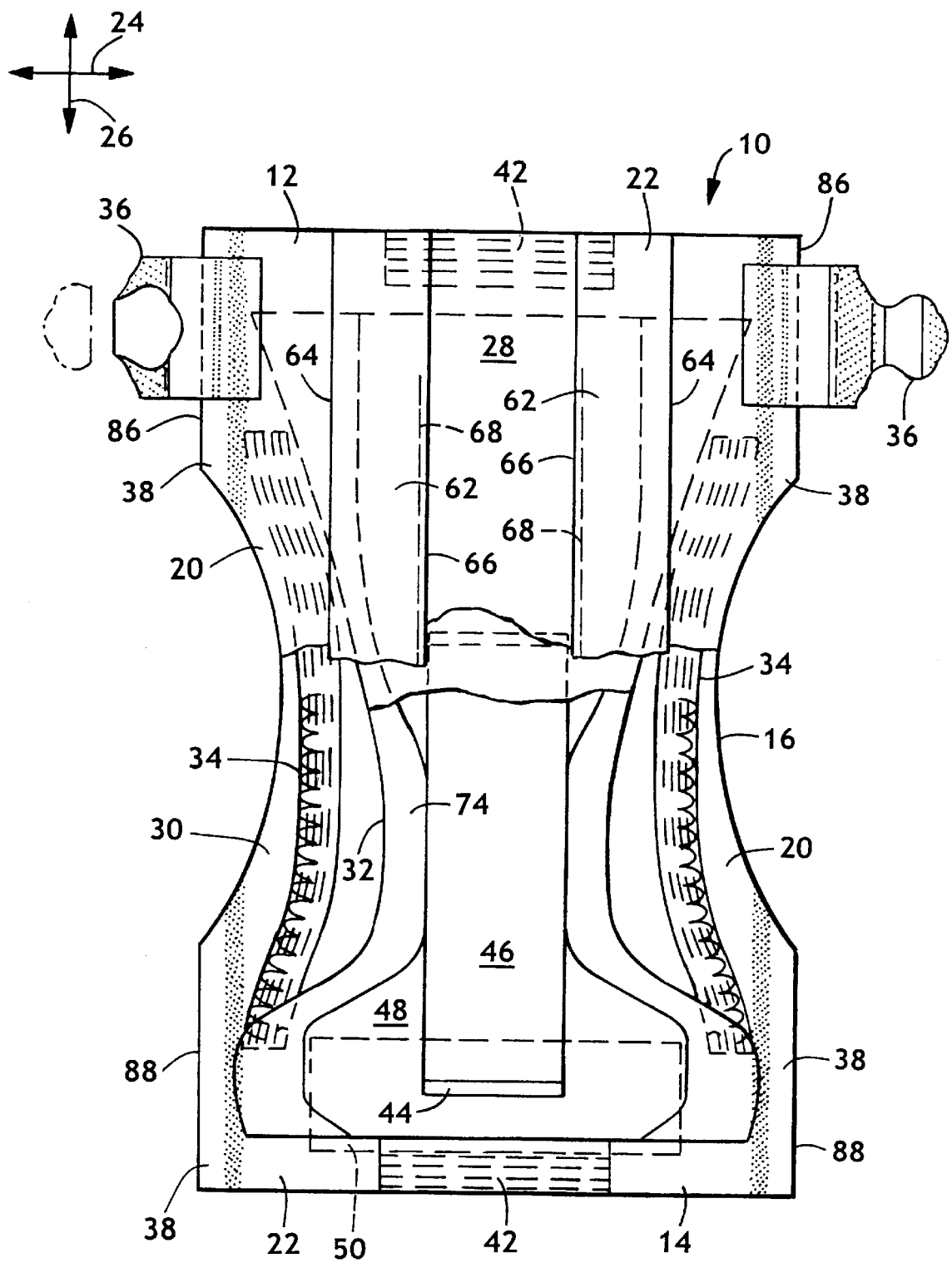
FIG. 1 representatively shows a partially cut-away, top plan view of a diaper article which incorporates the fastening system of the invention.
Figure 2:
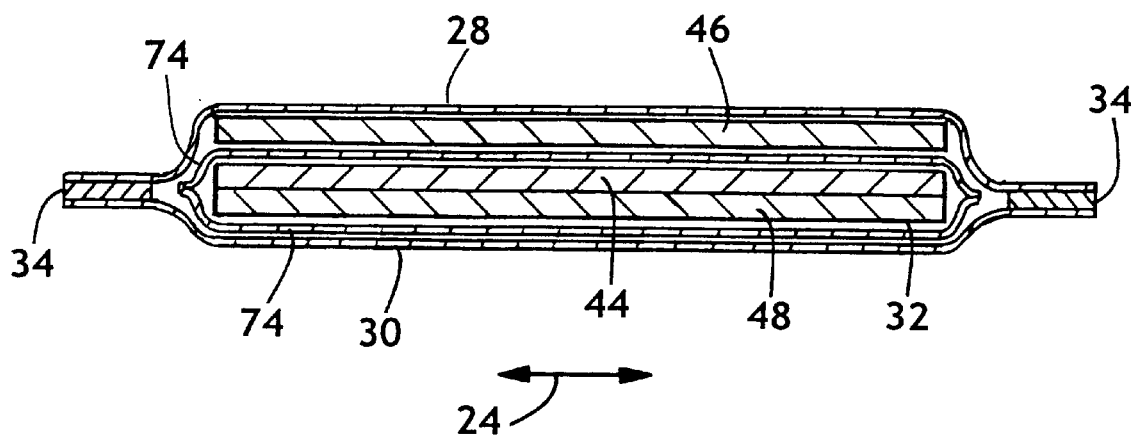
FIG. 2 representatively shows a schematic, lateral cross-sectional view of the article illustrated in FIG. 1.
Figure 3:
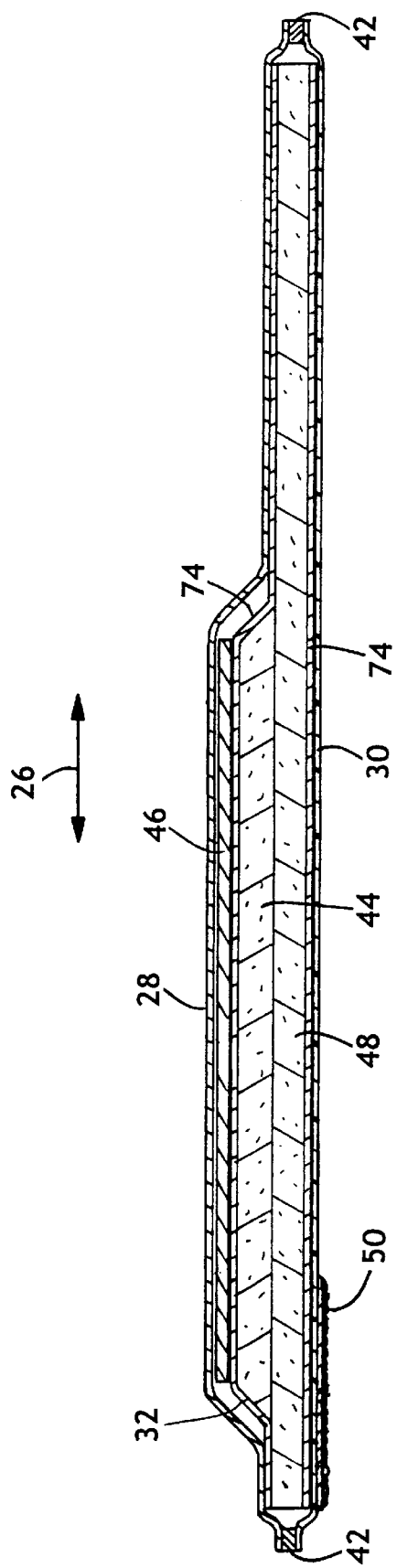
FIG. 3 representatively shows a schematic, longitudinal cross-sectional view of the article illustrated in FIG. 1.
Figure 4:
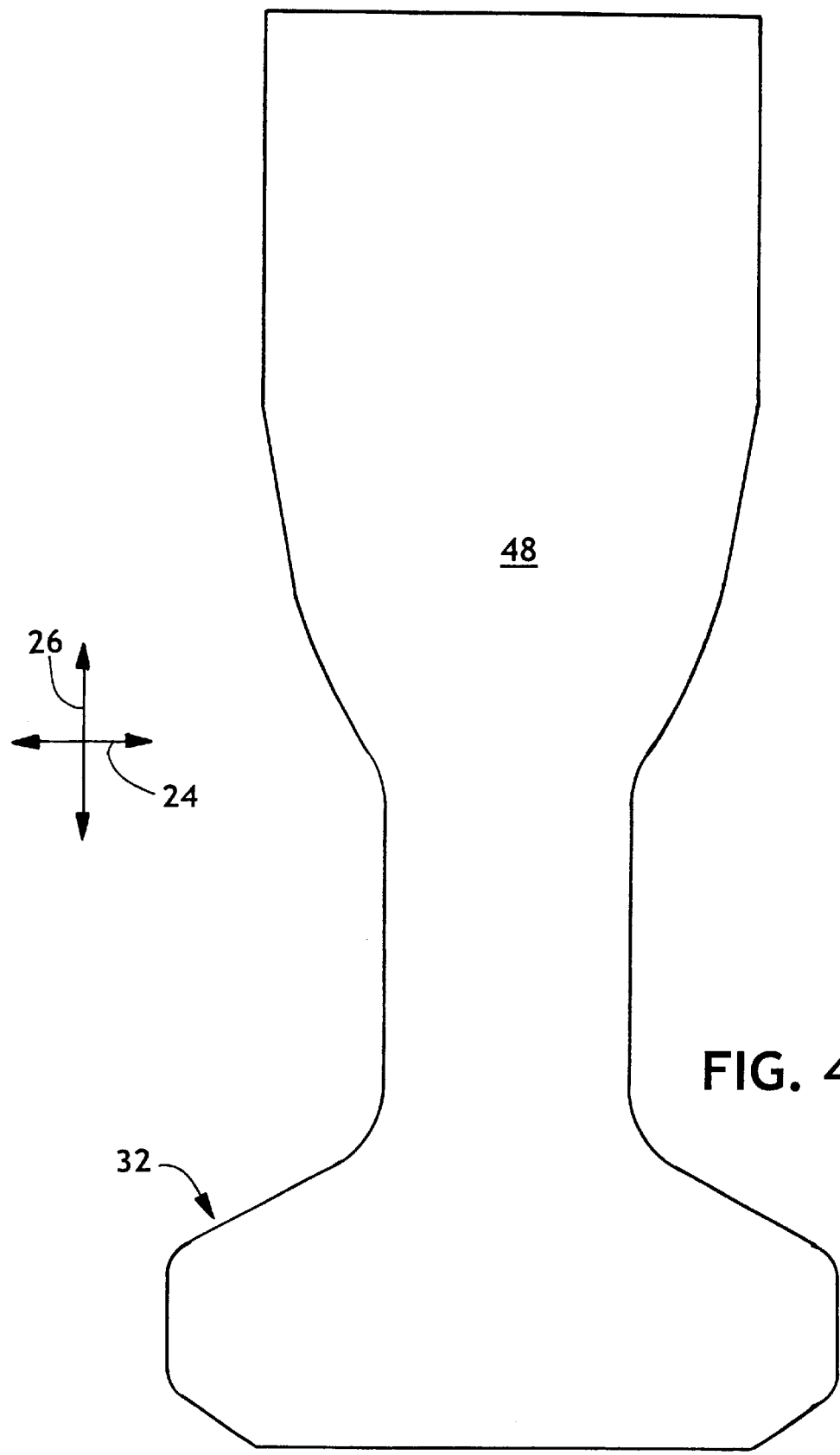
FIG. 4 representatively shows a top plan view of an absorbent body having the retention portion of the invention.
Figure 5:
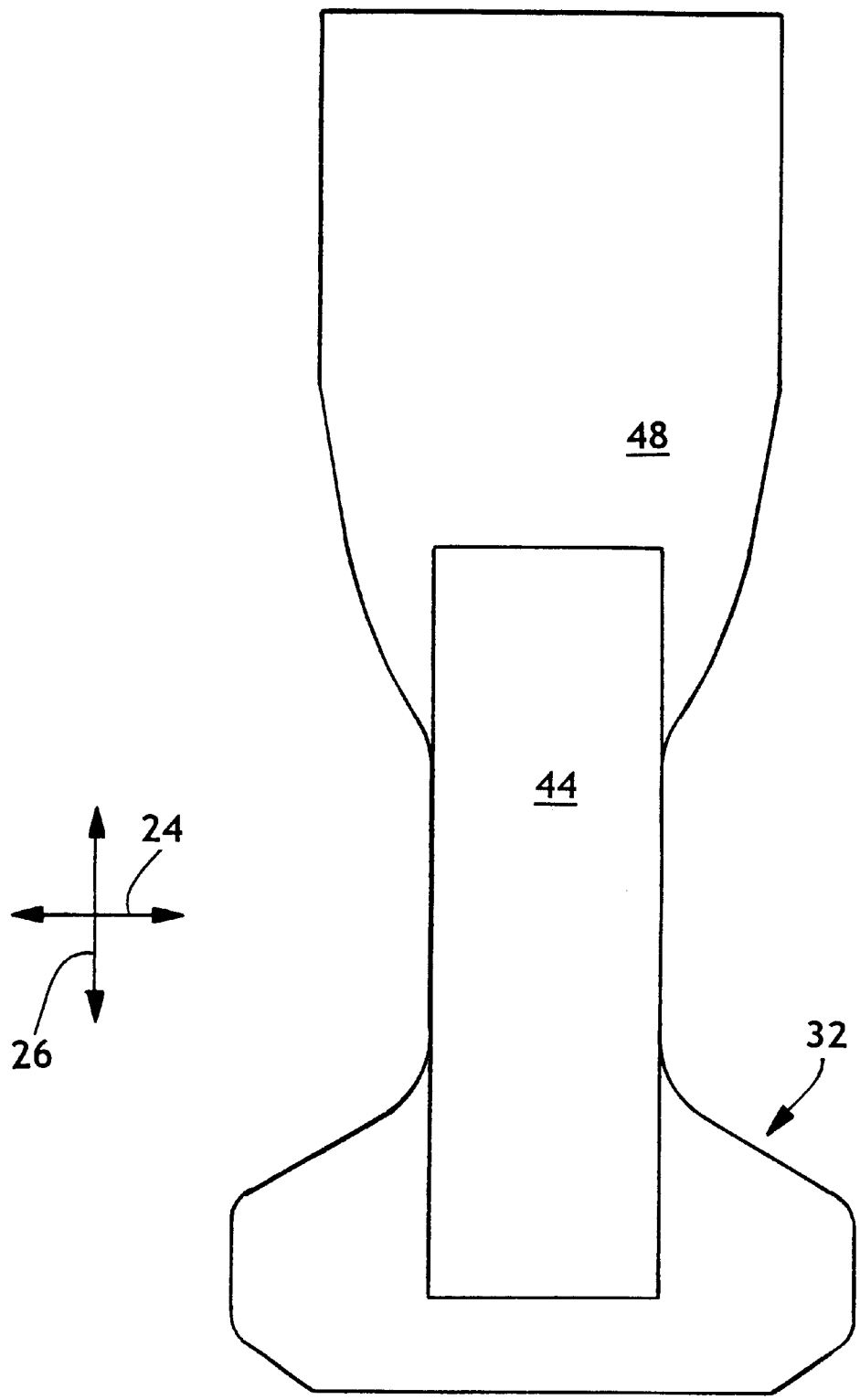
FIG. 5 representatively shows a top plan view of an absorbent body of the invention having a primary retention portion and a supplemental retention portion.
Figure 6:
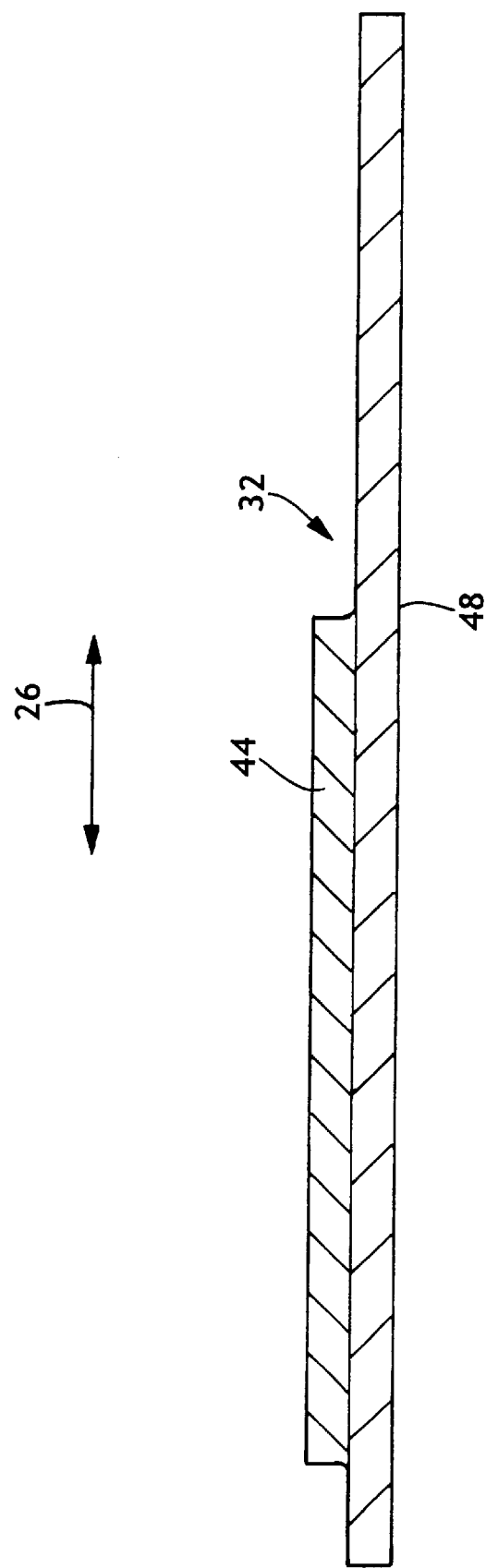
FIG. 6 representatively shows a longitudinal cross-section of the absorbent body of FIG. 5.

With reference to FIGS. 1, 2 and 3, an article, such as diaper 10 has a lengthwise, longitudinal direction 26, and a lateral, cross direction 24. The article includes a liquid permeable top sheet layer 28, a substantially liquid impermeable backsheet layer 30, and an absorbent structure, such as provided by an absorbent body structure 32, sandwiched between the top sheet and backsheet layers. The absorbent structure can include a primary retention portion 48, and the retention portion can include a wet-formed material. More particularly, the retention portion 48 can include a distinctive, wet-formed material which has a mixture of fibers and superabsorbent material. The absorbent material, particularly the wet-formed retention portion, can have selected properties, such as a selected edge-wise compression value, and a selected modified circular bend value. In desired aspects, the retention portion can have an edge-wise compression (per basis weight) value of not more than a maximum of about 9 g/gsm, and a wet, modified circular bend (per basis weight) value of at least minimum of about 0.3 g/gsm. In further aspects, the retention portion 48 can include cellulosic fibers, such as woodpulp fibers.

The article of the invention can, for example, be a garment provided by the representatively shown disposable diaper 10. The garment may also be a child care product, a feminine care product or an adult incontinence product. Examples of feminine care products are described in U.S. Pat. No. 3,881,490 entitled THIN, FLEXIBLE ABSORBENT PADS by H. A. WHITEHEAD et al. which issued May 6, 1975; U.S. Pat. No. 4,347,092 entitled PANTY LINER by J. J. HLABAN et al. which issued Aug. 31, 1982; U.S. Pat. No. 4,701,177 entitled THREE DIMENSIONAL SHAPED FEMININE PAD WITH NARROW, ABSORBENT CENTER AND WINGED EDGES by L. C. ELLIS et al. which issued Oct. 20, 1987; U.S. Pat. No. 5,401,267 entitled ABSORBENT ARTICLE HAVING ENHANCED WICKING CAPABILITY by L. COUTURE et al. which issued Mar. 28, 1995; and U.S. patent application Ser. No. 09/072, 172 entitled STABILIZED ABSORBENT MATERIAL AND SYSTEMS FOR PERSONAL CARE PRODUCTS HAVING CONTROLLED PLACEMENT OF VISCO-ELASTIC FLUIDS by A. S. BURNES which was filed May 5, 1998. The entire disclosures of these documents are incorporated herein by reference in a manner that is consistent herewith.

Examples of adult care, incontinence products are described in U.S. Pat. No. 5,669,901 to LaFortune et al. issued Sep. 23, 1997 and entitled ABSORBENT ARTICLE HAVING AN IMPROVED MECHANICAL FASTENING SYSTEM; U.S. Pat. No. 4,886,512 to Damico et al. issued Dec. 12, 1989 and entitled INCONTINENT GARMENT WITH ELASTICIZED POUCH; U.S. Pat. No. 4,315,508 to Bolick et al. issued Feb. 16, 1982 and entitled SELF-CENTERING MULTIPLE USE GARMENT SUSPENSION SYSTEM; U.S. Pat. No. 5,558,659 to Sherrod et al. issued Sep. 24, 1996 and entitled INCONTINENCE ARTICLE FOR MALES; and U.S. Pat. No. 4,500,316 to Damico issued Feb. 19, 1985 and entitled DISPOSABLE GARMENT. The entire disclosures of these documents are incorporated herein by reference in a manner that is consistent herewith.

Examples of child care products are described in U.S. Pat. No. 4,940,464 entitled DISPOSABLE INCONTINENCE GARMENT OR TRAINING PANT by P. T. VanGompel et al. which issued Jul. 10, 1990; U.S. Pat. No. 4,938,753 entitled SEAM CONSTRUCTION IN A DISPOSABLE TRAINING PANT, INCONTINENCE GARMENT, OR DIAPER by P. T. VanGompel et al. which issued Jul. 3, 1990; and U.S. Pat. No. 4,646,362 entitled DISPOSABLE UNDERPANTS, SUCH AS INFANTS' TRAINING PANTS AND THE LIKE by W. M. Heran which issued Mar. 3, 1987. The entire disclosures of these documents are incorporated herein by reference in a manner that is consistent herewith.

In desired aspects of the invention, the article can provide a first, rear or back waistband portion 12, and a second, front waistband portion 14. In addition, the article can have an intermediate or crotch portion 16 which interconnects between the first and second waistband portions 12 and 14, respectively. The diaper can further include a backsheet layer 30, a liquid permeable topsheet layer 28 connected and assembled in facing relation with the backsheet layer, and an absorbent structure, such as a structure which includes an absorbent body 32 having an appointed retention portion 48. The absorbent structure is sandwiched between the backsheet and topsheet layers, and is operably held therebetween. In addition, a fastening system, such as the system including fasteners 36, may be employed to interconnect the first waistband portion 12 with the second waistband portion 14 to hold the article on a wearer.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article has an appointed fastener landing zone member 50 which is disposed on the outward surface of the article.

In the configuration shown in FIGS. 1, 2 and 3, for example, the landing member 50 is disposed on the outward surface of the backsheet layer 30. The liquid permeable topsheet layer 28 is superposed in facing relation with the backsheet layer 30, and the absorbent body 32 is operably connected and affixed between the backsheet layer 30 and topsheet layer 28.

FIGS. 1, 2 and 3 show typical plan and cross-sectional views of the representative disposable diaper 10 in its generally flat-out, uncontracted state (i.e., with substantially all elastic induced gathering and contraction removed). In FIG. 1, the bodyside surface of the diaper which contacts the wearer is facing the viewer, and portions of the structure are partially cut away to more clearly show the interior construction of the diaper article. The outer edges of the diaper define a periphery with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article, the various inward or bodyside surfaces are configured to face toward the body of the wearer when the article is placed about the wearer. The designated outward surfaces of the article is configured to face away from the wearer's body when the article is placed about the wearer.

The diaper 10 can typically include a porous, liquid permeable topsheet 28; a substantially liquid impermeable backsheet 30; an absorbent body structure 32 positioned and connected between the topsheet and backsheet; a surge management portion 46 located adjacent the absorbent structure; and a system of elastomeric gathering members, such as a system including leg elastics 34 and waist elastics 42. The surge management portion is positioned in a liquid communication with an appointed storage or retention portion 48 of the absorbent structure, and the topsheet 28, backsheet 30, absorbent structure 32, surge management portion 46 and elastic members 34 and 42 may be assembled together into a variety of well-known diaper configurations. The diaper can additionally include a system of containment flaps 62, and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 6, 1993. Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER which issued Mar. 21, 1995; in U.S. patent application Ser. No. 286,086 of D. Fries, entitled A PROCESS FOR ASSEMBLING ELASTICIZED EAR PORTIONS and filed Aug. 3, 1994 which corresponds to U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 which corresponds to U.S. Pat. No. 5,595,618. The disclosures of the above-described documents are incorporated herein by reference in a manner that is consistent (not in conflict) herewith.

The diaper 10 generally defines the longitudinally extending length direction 26 and the laterally extending width direction 24, as representatively shown in FIGS. 1 and 2. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet and backsheet layers may not be coextensive. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated fluid surges typically occur in the diaper or other disposable absorbent article.

The backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. The backsheet 30 prevents the exudates contained in absorbent body 32 from wetting articles, such as bedsheets and overgarments, which contact diaper 10. In particular embodiments of the invention, the backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or non-woven fibrous web layer which has been totally or partially constructed or treated to impart the desired levels of liquid impermeability to selected regions that are adjacent or proximate the absorbent body. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6mil (0.015 mm) thick polypropylene blown film and a 0.7 ounce per square yard (23.8 gsm) polypropylene spunbond material (2 denier fibers). A material of this type forms the outercover of a HUGGIES SUPREME disposable diaper, which is commercially available from Kimberly-Clark Corporation. The backsheet 30 typically provides the outer cover of the article. Optionally, however, the article may include a separate outer cover component member which is additional to the backsheet.

The backsheet 30 may alternatively include a microporous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component such as the backsheet 30 or the containment flaps 62 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, 1978, or an equivalent thereof.

The size of the backsheet 30 is typically determined by the size of absorbent body 32 and the particular diaper design selected. Backsheet 30, for example, may have a generally T-shape, a generally I-shape or a modified hourglass shape, and may extend beyond the terminal edges of absorbent body 32 by a selected distance, such as a distance within the range of about 1.3 centimeters to 2.5 centimeters (about 0.5 to 1 inch), to provide at least a portion of the side and end margins.

The topsheet 28 presents a body-facing surface which is compliant, soft-feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 g/cm$^3$. The fabric can be surface treated with an operative amount of surfactant, such as about 0.28% TRITON X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet 28 to the backsheet 30. It should be readily appreciated that the above-described attachment means may also be employed to suitably interconnect, assemble and/or affix together the various other component parts of the articles which are described herein.

The absorbent body 32 provides an absorbent structure which can include a retention portion 48, such as the shown absorbent pad composed of selected hydrophilic fibers and high-absorbency particles, which holds and stores absorbed liquids and other waste materials. The absorbent body is positioned and sandwiched between the topsheet 28 and backsheet 30 to form the diaper 10. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 32 can comprise a matrix of hydrophilic fibers, such as a web of cellulosic fluff, mixed with particles of high-absorbency material, such as superabsorbent polymer material. In particular arrangements, absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may include absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the synthetic polymer material.

As mentioned previously, the high-absorbency material used in absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 100–900 gsm. In certain aspects of the invention, the average composite basis weight can be within the range of about 500–800 gsm, and alternatively can be within the range of about 550–750 gsm to provide desired performance.

The present invention can provide a distinctive absorbent structure which includes a wet-formed absorbent material constructed from liquid-containing precursor material which includes a mixture of fibers and superabsorbent particles. In particular aspects, the liquid includes water. The precursor desirably forms a liquid-borne slurry which contains the fiber and superabsorbent materials. For example, wet-laying techniques have typically produced an absorbent web from a precursor material composed of a mixture of fibers and superabsorbent particles combined with an operative liquid, such as water or other aqueous liquid. Other foam-forming techniques have processed the precursor material into a foam, and the foam has then been laid down to generate the desired web of absorbent material. For the purposes of the present description, the wet-laying techniques and the foam-forming techniques are collectively referred to as wet-forming techniques, and the resultant materials are referred to as wet-formed materials. The wet-formed absorbent materials are desirably not subjected to a subsequent fiberizing and/or airlaying process to form the retention portion 48.

Examples of suitable wet-formed materials and processes for making such materials are described in U.S. Pat. No. 5,651,862 entitled WET-FORMED ABSORBENT COMPOSITE by R. Anderson et al., which issued Jul. 29, 1997. The entire disclosure of this document is incorporated herein by reference in a manner that is consistent herewith.

In its various aspects and configurations, the absorbent structure of the invention can exhibit desirable physical properties, such as desired combinations of softness, flexibility and conformance in both its dry and wet states. When wet, the absorbent structure of the invention can advantageously resist separating, bunching and clumping. Since the absorbent structure can better retain its integrity when wet, it can resist becoming mushy and sagging, particularly in the crotch region of the product. As a result, the absorbent structures and articles of the invention can provide increased strength, improved fit, reduced leakage, and reduced clumping, bunching or sagging.

As previously described, the absorbent structure of the wet-formed material of the retention portion 48 can include a selected combination of fibrous material and superabsorbent material. In desired aspects, the composite wet-formed material has not been subjected to a fiberizing and/or airlaying procedure during the production of the retention portion. The fibrous material may include absorbent fibers, substantially nonabsorbent fibers, wettable fibers, substantially nonwettable fibers, cellulosic fibers, non-cellulosic fibers, natural fibers, or synthetic fibers, as well as combinations thereof. In particular aspects of the invention the structure of the retention portion 48 can include at least a minimum of about 0.5 wt % superabsorbent material, as determined with respect to the total weight of the dry retention portion. In selected products, such as articles configured for feminine care and light incontinence, the retention portion can alternatively include at least about 0.7 wt % superabsorbent material, and optionally, can include at least about 1 wt % superabsorbent material to provide improved benefits. In other selected products, such as articles configured for infant care diapers, child care training pants, and adult incontinence products, the retention portion can include at least about 15 wt % superabsorbent material, and optionally, can include at least about 30 wt % superabsorbent material to provide improved performance.

In other aspects of the invention, the absorbent structure of the wet-formed material of the retention portion 48 can include not more than a maximum of about 80 wt % superabsorbent material, as determined with respect to the total weight of the wet-formed material in the dry retention portion 48. In selected products, such as articles configured for feminine care and light incontinence, the wet-formed material of the retention portion can include not more than about 15 wt % superabsorbent material, and alternatively, can include not more than about 10 wt % superabsorbent to provide improved benefits. Optionally, the retention portion of such products can include not more than about 5 wt % superabsorbent material to provide desired benefits. In other selected products, such as articles configured for infant care diapers, adult incontinence garments and child care training pants, the wet-formed material of the retention portion can include not more than about 70 wt % superabsorbent material, and optionally, can include not more than about 60 wt % superabsorbent material to provide improved performance.

The wet-formed material of the retention portion 48 may or may not include a separately provided binder material, which is additional to the cellulosic fibers and superabsorbent polymer material. The amount of binder material in particular aspects of the invention can be at least about 0.001 wt %, as determined with respect to a total weight of the dry retention portion. In other aspects, the amount of binder material can be provided in an amount of not more than about 25 wt %.

Where the binder material is a wet-strength agent, the amount of binder material can be at least about 0.002 wt %, and can optionally be at least about 0.05 wt % to provide improved performance. In further aspects, the amount of wet-strength agent can be not more than about 2 wt %. Additionally, the amount of wet-strength agent can alternatively be not more than about 1 wt %, and optionally, can be not more than about 0.07 wt % to provide improved benefits.

Where the binder material is an adhesive binder, the amount of binder material can be at least about 0.05 wt %. The amount of adhesive binder can alternatively be at least about 1 wt %, and optionally, can be at least about 5 wt % to provide improved performance. In additional aspects, the amount of adhesive binder can be not more than about 25 wt %. The amount of adhesive binder can alternatively be not more than about 20 wt %, and optionally, can be not more than about 15 wt % to provide improved benefits.

Where the binder material is an activated binder fiber, such as a thermoplastic fiber or a solvent activated fiber, the amount of binder fiber can be at least about 1 wt %. The amount of binder fiber can alternatively be at least about 1.5 wt %, and optionally, can be at least about 2 wt % to provide improved performance. In additional aspects, the amount of binder fiber can be not more than about 25 wt %. The amount of binder fiber can alternatively be not more than about 15 wt %, and optionally, can be not more than about 5 wt % to provide improved benefits.

Where the binder material is a plasticizer, the amount of plasticizer can be at least about 1 wt %. The amount of plasticizer can alternatively be at least about 1.5 wt %, and optionally, can be at least about 2 wt % to provide improved performance. In additional aspects, the amount of plasticizer can be not more than about 25 wt %. The amount of plasticizer can alternatively be not more than about 15 wt %, and optionally, can be not more than about 5 wt % to provide improved benefits.

Another aspect of the present invention can include a retention portion 48 having wet-formed material which contains stiffened cellulose fibers in an amount which is at least about 20 wt % of the total amount of fibrous material in the retention portion. The amount of stiffened cellulose fibers can alternatively be at least about 30 wt %, and can optionally be at least about 40 wt % to provide improved performance. In further aspects, the wet-formed material of the retention portion 48 can contain stiffened cellulose fibers in an amount which is not more than about 100 wt % of the total amount of fibrous material in the retention portion. The amount of stiffened cellulose fibers can alternatively be not more than about 70 wt %, and can optionally be not more than about 60 wt % to provide improved performance.

Another aspect of the invention can include a wet-formed retention portion 48 which may contain substantially no fiber composed of hydrophilic, crimped, synthetic polymer material. The wet-formed material of the retention portion may alternatively contain at least about 5 wt % of hydrophilic, crimped, synthetic fiber, as determined with respect to a total amount of fibrous material in the retention portion, and may optionally contain at least about 10 wt % of hydrophilic, crimped, synthetic fiber to provide improved performance. In still other aspects, the retention portion may contain not more than about 50 wt % of hydrophilic, crimped, synthetic fiber. The retention portion may alternatively contain not more than about 25 wt % of hydrophilic, crimped, synthetic fiber, and may optionally contain not more than about 20 wt % of hydrophilic, crimped, synthetic fiber to provide improved performance. The synthetic fiber can have a fiber length greater than about 2 mm.

In desired aspects, the wet-formed material of the retention portion 48 can have a dry thickness which is at least a minimum of about 0.5 mm, as determined under a restraining pressure of 1.38 KPa. The dry thickness can alternatively be at least about 0.7 mm, and can optionally be at least about 1 mm to provide improved performance. In further aspects, the retention portion 48 can have a dry thickness which is not more than a maximum of about 30 mm. The dry thickness can alternatively be not more than about 20 mm, and can optionally be not more than about 10 mm to provide improved benefits.

In still other aspects, the wet-formed material of the retention portion 48 can have a dry density which is at least a minimum of about 0.02 g/cm$^3$ as determined under a restraining pressure of 1.38 KPa. The dry density can alternatively be at least about 0.05 g/cm$^3$, and can optionally be at least about 0.1 g/cm$^3$ to provide improved performance. Additionally, the retention portion 48 can have a dry density which is not more than a maximum of about 0.6 g/cm$^3$. The dry density can alternatively be not more than about 0.5 g/cm$^3$, and can optionally be not more than about 0.35 g/cm$^3$ to provide improved benefits.

The wet-formed material of the retention portion 48, in still further aspects, can have a dry tensile strength value which is at least a minimum of about 0.7 Newtons per cm of width (N/cm), as determined by tensioning along the longitudinal direction 26 of the article. The dry tensile strength can alternatively be at least about 1 N/cm, and can optionally be at least about 1.5 N/cm to provide improved performance. Additionally, the wet-formed retention portion 48 can have a dry tensile strength value which is not more than a maximum of about 20 N/cm, as determined along the longitudinal direction of the article. The dry tensile strength can alternatively be not more than about 10 N/cm, and can optionally be not more than about 5 N/cm to provide improved benefits.

The selected compositions of the retention portion 48, as described herein, can advantageously help to increase the strength, softness and flexibility of the wet-formed material in the retention portion. In particular, an appropriate choice of the constituent materials in the retention portion can help provide a desired combination of strength and softness. For example, adding stiffened, crosslinked cellulose fibers to the web can impart bulk and softness. Increasing the amount of superabsorbent can also impart softness by reducing fiber-to-fiber bonding.

With reference to FIGS. 1, 2, 3, 5 and 6, the absorbent article can further include a supplemental absorbent layer 44. The supplemental layer 44 may extend over only a selected portion of the area of the retention portion, as representatively shown, or may extend over the entire area of the retention portion 48. Where the supplemental layer provides an intake or distribution layer, the distribution or intake layer can contain a matrix of fibers, such as cellulosic, wood pulp fluff fibers, with substantially no superabsorbent material. Alternatively, the distribution or intake layer can contain at least about 2 wt % of superabsorbent polymer material, as determined with respect to a total weight of the supplemental, distribution or intake layer, and may optionally contain at least about 5 wt % of superabsorbent material to provide improved benefits. Additionally, the amount of superabsorbent material in the distribution or intake layer can be not more than about 50 wt %. The amount of superabsorbent material in the distribution or intake layer can alternatively be not more than about 40 wt %, and optionally can be not more than about 25 wt % to provide improved performance. The distribution or intake layer can also be positioned on a body side or an outward side of the primary retention portion 48, as desired.

Where the supplemental layer 44 provides a supplemental retention layer, the supplemental retention layer can contain a mixture of wood pulp fluff fibers with at least about 30 wt % of superabsorbent material. Alternatively, the supplemental retention layer can contain at least about 35 wt % of superabsorbent polymer material, as determined with respect to a total weight of the supplemental retention layer, and may optionally contain at least about 40 wt % of superabsorbent material to provide improved benefits. Additionally, the amount of superabsorbent material in the supplemental retention layer can be not more than about 80 wt %. The amount of superabsorbent material in the supplemental retention layer can alternatively be not more than about 70 wt %, and optionally can be not more than about 60 wt % to provide improved performance. Also, the supplemental retention layer can be positioned on a body side or an outward side of the primary retention portion 48, as desired.

The wet integrity of the absorbent material, particularly the wet-formed absorbent material, can be shown by a modified circular bend (MCB) value. In particular aspects, the wet-formed absorbent material can have a wet MCB, per dry basis weight, value (wet MCB value) of at least a minimum of about 0.3 g/gsm. Alternatively, the wet-formed absorbent material can have a wet MCB value of at least about 0.4 g/gsm, and optionally, the wet-formed absorbent material can have a wet MCB value of at least about 0.5 g/gsm to provide improved performance. When the absorbent material exhibits a MCB value of less than about 0.3 g/gsm, the material has little wet integrity and tends to separate and bunch and clump during use.

In other aspects, the wet-formed absorbent material can have a wet MCB value of not more than a maximum of about 3 g/gsm. Alternatively, the wet-formed absorbent material can have a wet MCB value of not more than about 2 g/gsm, and optionally, the wet-formed absorbent material can have a wet MCB value of not more than about 1 g/gsm to provide further benefits.

The wet MCB value can be determined with a modified circular bend test method. In this test, a probe is pushed into the sample and the load measured as a function of distance into the sample. This is similar to how consumers typically test for the degree of saturation of the diaper by pushing on the general area of the front panel or crotch area of the diaper. Using the test method described in detail herein, the wet MCB value of a material reflects an average of the wet integrity of the absorbent material in all directions.

Wet MCB Value

The wet integrity of a material can be determined by a test which is modeled after the ASTM D4032-82 Circular Bend Procedure. A modified test is used for the purposes of the present invention, and is hereinafter referred to as the "Wet Modified Circular Bend Procedure". The Wet Modified Circular Bend Procedure provides a simultaneous, multi-directional deformation of a material during which one face of a material becomes concave and the other face becomes convex. The Wet Modified Circular Bend Procedure gives a force value which relates to the stiffness of the material, simultaneously averaging stiffness in all directions, and is herein as being related to the wet integrity of the material.

The apparatus employed for the Wet Modified Circular Bend Procedure is a modified Circular Bend Stiffness Tester, having the following parts: A smooth-polished metal plate platform which is 102.0 millimeters (length) by 102.0 millimeters (width) by 6.35 millimeters (depth) having a 18.75 millimeter diameter orifice. The lap edge of the orifice should be at a 45 degree angle to a depth of 4.75 millimeters. A plunger having the following dimensions is used: overall length of 60 millimeters, a diameter of 6.25 millimeters, a ball nose having a radius of 2.97 millimeters and a needle-point extending about 1 millimeter from the ball nose with a 0.33 millimeter base diameter and a point having a radius of less than 0.5 millimeters. The plunger is mounted concentrically with the orifice having equal clearance on all sides. The needle-point is used merely to prevent lateral movement of a sample during testing. The bottom of the plunger should be set well above the top of the orifice plate. From this position, the downward stroke of the ball nose is to the exact bottom of the plate orifice.

A load cell having a load range of from about 0.0 to about 4500 grams was used as a force measurement gauge. The compression tester used was a SINTECH 500/S with a MTS Part # 27.00098-5 lb load cell, or a MTS Part # 27.00099-10 lb load cell. The load cells are available from MTS Systems Corporation, a business having offices located in Eden Prairie, Minn. 55344. After calibrating the load cell, the gage length for displacement of the plunger was set to 25.4 mm from the base of the ball nose of the plunger to the bottom of the orifice plate.

To conduct the test, an absorbent sample was cut into a 38.1 mm×38.1 mm square specimen. The sample was weighed on an electronic balance in a Petri dish. 10.0 to 10.5 g/g of 0.9% saline was added to the sample with a small pipette or eye dropper. The liquid is added to the top of the sample so that the liquid is evenly spread on the sample. After 20–25 minutes equilibration time after fluid addition, the sample was centered onto the test platform and the plunger was lowered down on the specimen for a 25.4 mm gage length at a crosshead speed of 500 mm/min. During the movement of the plunger, the absorbent sample is deflected downward into the 18.75 mm hole by the plunger and the maximum force exerted by the compression tester to deflect the sample during the 25.4 mm gage length displacement of the plunger is measured by the load cell and recorded. The force measured by the load cell divided by the dry basis weight of the specimen is reported in units of grams force/grams per square meter of specimen (g/gsm). This value is used as the Wet MCB value to obtain a quantitative measure of the wet integrity of the specimen. The higher the Wet MCB value (e.g. g/gsm), the greater the integrity of the specimen.

The softness and flexibility of the absorbent material, particularly the wet-formed absorbent material, can be shown by an Edge-wise Compression (EC) value which reflects the softness or stiffness of the dry absorbent material. Accordingly, the Edge-wise Compression value can also reflect the flexibility or stiffness of the absorbent article between the legs of the wearer, and can provide an important indication of desired comfort and fit.

In particular aspects, the absorbent material can have an Edge-wise Compression, per dry basis weight, value (EC value) of not more than a maximum of about 9 g/gsm, where the basis weight is expressed grams per square meter (gsm, or $g/m^2$). Alternatively, the absorbent material can have a EC value of not more than about 6 g/gsm, and optionally, the absorbent material can have a EC value of not more than about 3 g/gsm to provide improved performance. If the EC value is greater than about 9 g/gsm, the dry absorbent material and the corresponding absorbent article can be too stiff.

For particular configurations, such as infant care and child care products, the absorbent material can have an edge-wise Compression, per dry basis weight, value (EC value) of not more than a maximum of about 3 g/gsm, where the basis weight is expressed grams per square meter (gsm or $g/m^2$). Alternatively, the absorbent material can have a EC value of not more than about 2 g/gsm, and optionally, the absorbent material can have a EC value of not more than about 1 g/gsm to provide desired performance. If the EC value for such products is greater than about 3 g/gsm, the dry absorbent material and the corresponding absorbent article can again be too stiff.

In other aspects of the invention, the absorbent material can have an EC divided by basis weight value (EC value) of at least a minimum of about 0.3 g/gsm. Alternatively, the absorbent material can have a EC value of at least about 0.4 g/gsm, and optionally, the absorbent material can have a EC value of at least about 0.5 g/gsm to provide further benefits.

Edge-wise Compression Value

The method by which the Edge-wise Compression (EC) value can be determined is set forth below. A 2 inch by 12 inch (5.1 cm×30.5 cm) piece of absorbent material is cut with its longer dimension aligned with the longitudinal direction of the product or raw material web. The weight of the sample is determined. The thickness of the material is determined under a 0.2 psi ( 1.38 KPa) load. The material is formed into a cylinder having a height of 2 inches (5.1 cm), and with the two ends having 0–0.125 inch (0–3.18 mm) overlap, the material is stapled together with three staples. One staple is near the middle of the width of the product, the other two nearer each edge of the width of the material. The longest dimension of the staple is in the circumference of the formed cylinder to minimize the effect of the staples on the testing.

An INSTRON tester, or similar instrument is configured with a bottom platform, a platen larger than the circumference of the sample to be tested and parallel to the bottom platform, attached to a compression load cell placed in the inverted position. The specimen is placed on the platform, under the platen. The platen is brought into contact with the specimen and compresses the sample at a rate of 25 mm/min. The maximum force obtained in compressing the sample to 50% of its width (1 inch) (2.54 cm) is recorded.

If the material buckles, it is typical for the maximum force to be reached before the sample is compressed to 50%. In a product where the length of the absorbent is less than 12 inches (30.5 cm), the EC value of the material can be determined in the following manner. A detailed discussion of the edge-wise compression strength has been given in *The Handbook Of Physical And Mechanical Testing Of Paper And Paperboard*, Richard E. Mark editor, Dekker 1983, (Vol. 1). Based on theoretical models governing buckling stresses, in the Edge-wise Compression configuration described, the buckling stress is proportional to $E*t^2/(H^2)$ with the proportionality constant being a function of $H^2/(R*t)$ where E is the Elastic modulus, H is the height of the cylinder, R is the radius of the cylinder, and t is the thickness of the material. Expressing the stress in terms of force per basis weight, it can be shown that the parameter that needs to be maintained constant is $H^2/R$. Therefore, for a sample that is smaller than 12 inches (30.5 cm), the largest possible circle should be constructed and its height (width of the sample being cut out) adjusted such that $H^2/R$ equals 2.1 inches (5.3 cm).

To improve the containment of the high-absorbency material, absorbent body structure 32 can include an overwrap, such as a wrap sheet 74, which is placed immediately adjacent and around the absorbent body 32 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of the absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of the absorbent body 32. Such a configuration of the wrap sheet can, for example, facilitate the formation of a substantially complete sealing and closure around the peripheral edges of the absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of the absorbent wrap 74 can extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of the wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

The article, such as diaper 10, can also include a surge management layer 46 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. In the illustrated embodiment, for example, the surge layer 46 can be located on an inwardly facing body side surface of topsheet layer 28. Alternatively, the surge layer 46 may be located adjacent to an outer side surface of topsheet 28. Accordingly, the surge layer would then be interposed between topsheet 28 and absorbent body 32. Examples of suitable surge management layers 46 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 which corresponds to U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 which corresponds to U.S. Pat. No. 5,490,846. Other suitable surge management materials are described in U.S. patent application Ser. No. 754,417 filed Nov. 22, 1996 and entitled HETEROGENEOUS SURGE MATERIAL FOR ABSORBENT ARTICLES by R. Dodge et al. The entire disclosures of these documents are hereby incorporated by reference in a manner that is consistent herewith.

The article of the invention may or may not include leg elastic members 34. Where the leg elastic members are included, the leg elastic members 34 can be located in the lateral side margins of the article. In the shown diaper 10, for example, the leg elastic members are assembled into the lateral side margins 20, and are arranged to draw and hold the diaper against the legs of the wearer. The elastic members are secured to the diaper in an elastically contractible condition so that in a normal under strain configuration, the elastic members effectively contract against the diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other mechanisms, such as heat-shrink elastic material, may be used to gather the garment.

In the embodiment illustrated in FIGS. 1 and 2, the leg elastic members 34 extend essentially along the complete length of the intermediate crotch region 16 of diaper 10. Alternatively, the elastic members 34 may extend the entire length of diaper 10, or any other length suitable for providing the arrangement of elastically contractible lines desired for the particular diaper design.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to the diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Delaware. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (FIG. 1).

In the various configurations of the invention, the ear regions may be integrally formed with a selected diaper component. For example, the ear regions 38 can be integrally formed from the layer of material which provides the backsheet layer 30, or may be integrally formed from the material employed to provide the topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along a ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The illustrated ear regions have a tapered, curved or otherwise contoured shape in which the longitudinal length of the relatively inboard base region is larger or smaller than the longitudinal length of its relatively outboard end region. Alternatively, the ear regions may include a substantially rectangular shape, and optionally may include a substantially trapezoidal shape.

The article, such as the shown diaper 10, can also include a pair of elasticized containment flaps 62 which extend generally length-wise along the longitudinal direction 26 of the diaper. The containment flaps are typically positioned laterally inboard from the leg elastics 34, and substantially symmetrically placed on each side of the lengthwise, longitudinal centerline of the diaper. In the illustrated arrangements, each containment flap 62 has a substantially fixed edge portion 64 and a substantially movable edge portion 66, and is operably elasticized to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT, which corresponds to U.S. Pat. No. 5,562,650, the disclosure of which is hereby incorporated by reference in a manner that is consistent herewith.

In optional, alternative configurations of the invention, diaper 10 may include internal, elasticized, containment waist flaps, such as those described in U .S. Pat. No. 4,753,646 issued Jun. 28, 1988, to K. Enoe, and in U.S. patent application Ser. No. 560,525 of D. Laux et al. entitled AN ABSORBENT ARTICLE WITH IMPROVED ELASTIC MARGINS AND CONTAINMENT SYSTEM and filed Dec. 18, 1995, the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid.

To provide a desired refastenable fastening system, the article representatively shown by diaper 10 can include one or more, appointed landing member regions or patches, such as provided by the representatively shown, primary landing member 50. The landing member can provide an operable target area for generating a releasable and re-attachable securement with at least one of the fastener tabs 36. In desired embodiments of the invention, the landing member patch can be positioned on the front waistband portion 14 of the diaper and located on the outward surface of the backsheet layer 30. Alternatively, the landing member patch can be positioned on an appointed inward surface of the diaper, such as the bodyside surface of the topsheet layer 28.

Particular arrangements of the invention can include one or more landing members 50 which can be directly or indirectly attached to the second waistband portion 14. Desirably, the landing members are affixed directly to the outward surface of the appropriate waistband portion, but may optionally be joined to the inward, bodyside surface of the article waistband portion.

In the various configurations of the invention, the landing member 50 can be composed of a substantially non-elastomeric material, such as polymer films or tapes, woven fabrics, nonwoven fabrics or the like, as well as combinations thereof. In particular configurations of the invention, the landing member may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

The various configurations of the invention can include at least one separately provided fastener tab 36 located at either or both of the lateral end regions 86 of the back waistband 12. Alternatively, the at least one separately provided fastener tab 36 can be located at either or both of the lateral end regions 88 of the front waistband 14. The representatively shown embodiment, for example, has a laterally opposed pair of the fastener tabs 36 with a one of the fastener tabs located at each of the distal side edges of the rear waistband 12. More particularly, each of the fasteners 36 is assembled and attached to project and extend from a corresponding, immediately adjacent ear region located at one of the opposed, lateral end regions 86 of the front waistband section 12.

The fastener tab 36 can be composed of a substantially non-elastomeric material, such as polymer films or tapes, woven fabrics, nonwoven fabrics or the like, as well as combinations thereof. Optionally, the fastener tab may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

In the various aspects and configurations of the invention, the fastening mechanism between the selected first fastener component and the selected, second fastener component may be adhesive, cohesive, mechanical or combinations thereof. In the context of the present invention, a mechanical fastening system is a system which includes cooperating, first and second components which mechanically inter-engage to provide a desired securement.

Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated arrangements, for example, the mechanical fastening system may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a selectively releasable, interengaging mechanical fastening system can, for example, locate the first fastener component on at least the appointed mating or securing surface of the fastener tab 36, and can locate the cooperating, second fastener component on the appointed engagement surface of the appointed landing member 50. For example, with the representatively shown hook-and-loop fastener, the fastening component which is attached to the appointed mating or securing surface of the fastener tab 36 may include a hook type of mechanical fastening element, and the complementary fastening component, which is operably joined and attached to the appointed landing zone member 50 can include a loop type of fastening element.

It should also be readily apparent that, in the various configurations of the invention, the relative positions and/or materials of the first fastening component and its cooperating, complementary second fastening component can be transposed. Accordingly, the fastening component, which is attached to the appointed mating surface of the fastener tabs 36, may include a loop type of mechanical fastening element; and the complementary, second fastening component, which is operatively joined and attached to the appointed landing zone member, can include a hook type of fastening element.

Examples of hook-and-loop fastening systems and components are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. which corresponds to U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 which corresponds to U.S. Pat. No. 5,624,429 which issued Apr. 29, 1997, the entire disclosure of which is hereby incorporated by reference in a manner which is consistent herewith.

Each fastener tab 36 can have a variety of rectilinear or curvilinear shapes and planforms, as well as combinations thereof. For example, as illustrated in the representatively shown arrangements, the fastener tab can have a contoured, bell-shape. Alternatively, the fastener tab can have a quadrilateral, generally rectangular shape. In addition, the longitudinally extending, laterally outward, terminal edge of the fastener tab may be substantially straight. Optionally, the longitudinally extending, laterally outward, terminal edge of the fastener tab may have only a limited amount of waviness.

In the various configurations of the invention, the desired first fastener component can be a hook material which provides hook-type engagement members. An example of a suitable hook material is a micro-hook material which is distributed under the designation VELCRO HTH 829, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units). Other suitable hook materials can include VELCRO HTH 858, VELCRO HTH 851 and VELCRO HTH 863 hook materials.

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensboro, N.C. under the trade designation #34285, as well other of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

The loop material may also include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. patent application Ser. No. 754,419 entitled PATTERN-UNBONDED NONWOVEN WEB AND PROCESS FOR MAKING THE SAME, by T. J. Stokes et al., and filed Dec. 17, 1996; the entire disclosure of which is incorporated herein by reference in a manner that is consistent herewith.

In the various configurations of the invention, the loop material need not be limited to a discrete or isolated patch on the outward surface of the article. Instead, the loop material can, for example, be provided by a substantially continuous, outer fibrous layer which is integrated to extend over substantially the total exposed surface area of a cloth-like outer cover employed with the desired article.

In the various arrangements of the invention, the engagement force between the selected first fastener component and its appointed and cooperating second fastener component should be large enough and durable enough to provide an adequate securement of the article on the wearer during use. In particular arrangements, especially where there are sufficiently high levels of engagement shear force provided by the fastening system, the fastening engagement may provide a peel force value of not less than a minimum of about 40 grams-force (gmf) per inch of the "width" of engagement between the first and second fastener components. In further arrangements, the fastening engagement may provide a peel force value of not less than about 100 gmf/inch to provide improved advantages. In desired configurations, the fastening engagement may provide a peel force value of not less than about 200 gmf per inch of the "width" of engagement between the first and second fastener components . Alternatively, the peel force is not less than about 300 gmf/inch, and optionally is not less than about 400 gmf/inch to further provide improved benefits. In other aspects, the peel force is not more than about 1,200 gmf/ inch. Alternatively, the peel force is not more than about 800 gmf/inch, and optionally is not more than about 600 gmf/inch to provide improved performance.

The engagement force between the selected first fastener component and its appointed and cooperating second fastener component may additionally provide a shear force value of not less than about 400 gmf per square inch of the area of engagement between the first and second fastener components. Alternatively, the shear force is not less than about 1,000 gmf/in$^2$, and optionally, is not less than about 1,700 gmf/in$^2$. In further aspects, the shear force can be up to about 4,400 gmf/in$^2$, or more. Alternatively, the shear force is not more than about 3,900 gmf/in$^2$, and optionally is not more than about 3,500 gmf/in$^2$ to provide improved performance.

Desirably, the securing engagement between the first and second fastener components should be sufficient to prevent a disengagement of the fastener tab 36 away from the landing member 50 when the fastener tab 36 is subject to a tensile force of at least about 3,000 grams when the tensile force is applied outwardly along the lateral direction, aligned generally parallel with the plane of the backsheet layer 30 of the article.

Each of the fastener components and fastening elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with their associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by co-extruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing member of the article.

The following Examples are presented to provide a more detailed understanding of the invention, and are not intended to limit the scope of the invention.

EXAMPLES

Wet-laid, superabsorbent-containing, composite materials in the following Examples were prepared with the following technique. The fiber furnish was prepared by hydropulping together the regular and crosslinked, cellulose pulps (bleached southern softwood kraft pulp CR0054 from Kimberly-Clark Corp.; bleached eucalyptus kraft pulp from Aracruz Cellulose SA; and NHB416 crosslinked pulp from Weyerhaeuser Corp.). Generally stated, the hydropulping process includes a dispersing of the fibrous material in water, and an agitation of the resulting mixture. The hydropulping was conducted at an ambient room temperature to a 3% consistency. If a wet-strength agent or binder material, such as KYMENE binder, was added, it was done at the hydropulping stage. For example, KYMENE binder can be added in the amount of 10 pounds of KYMENE binder solids per 1 metric ton of furnish. Because of the difficulty of opening the crosslinked fibers, the hydropulping was normally done for one hour. A suitable device for hydropulping the fibrous materials is a 10 gallon, laboratory model, hydropulper available from Adirondack Machine Corp, a business having offices located in Glen Falls, N.Y., or a substantially equivalent system.

The handsheets were formed using a SERIES 9000 computerized handsheet former, available from M/K Systems, a business having offices in Danvers, Mass. The forming wire fabric in the forming chamber of the handsheet former was composed of 90×90 mesh, stainless steel.

The handsheet forming process included a pumping of about one gallon of fresh water into the forming chamber (about 1 second of flow). Sufficient furnish was pumped into the forming chamber to provide the final handsheet (with superabsorbent) with a basis weight of about 400 gsm (g/m$^2$). Additional water was added to dilute the resulting stock. If it was desirable to slow the swelling of the superabsorbent polymer (SAP) material, this additional water was composed of ice water (at a temperature of 2° C.). The fiber was thoroughly agitated in the forming chamber, and superabsorbent polymer material was added during the agitation. The addition of the superabsorbent occurred at the beginning of the agitation, if a large amount of superabsorbent swelling was desirable; and occurred near the end of the agitation, if a small amount of superabsorbent swelling was desirable. The contents of the forming chamber were allow to settle for 2 seconds, and were then drained. The resulting sheet was de-watered, and then dried at a temperature of 105° C.

Sheets with sufficiently high integrity could be automatically de-watered by the former, then picked off the felt in the former and placed on a stainless steel screen for oven drying. The sheets can, for example, be de-watered with a vacuum de-watering system. Sheets which did not have enough integrity to be automatically de-watered were handled manually. During the manual handling, the automated process was paused at the drainage stage, and the handsheet was further consolidated with blotters and a rolling weight. The sheet was then transferred by hand from the forming screen directly onto a drying screen.

Examples of wet, foam-formed composite materials constructed from a foamed fiber slurry were produced with the following technique. The foam-forming technique employed the equipment and procedures employed to produce the wet-laid absorbent composite materials, except that at the stage where the fiber slurry is agitated in the forming chamber, the equipment was placed on hold—that is the agitation was continued until a command was entered to stop it. Particulate superabsorbent polymer material was added to the forming chamber, followed by an addition of 9.5 wt % of surfactant, based on the combined dry weight of fiber and superabsorbent. The surfactant used was REXENE KB obtained from ICI Surfactants, a business having offices located in Wilmington, Del. The resultant superabsorbent polymer and fiber slurry foamed vigorously due to the air bubble agitation. A hand mixer was used to break the large bubbles into a finer, more uniform foam. When the slurry appeared stable (after approximately 45 seconds of agitation), drainage was begun. The formed sheet was extremely weak and was lifted off the wire by sliding a sheet of polypropylene spunbonded fabric between the wire and the composite and using this fabric to support the formed sheet during the transfer to a drying rack. Drying was conducted at a temperature of 105° C., as noted above for the wet-laid absorbent materials.

In many of the examples, the various wet-formed samples, as prepared, were too stiff for purposes of the present invention. Accordingly, the excessively stiff materials were further modified by various softening methods. These methods included a humidification of the materials, a mechanical softening through a nip between a pair of matched grooved rolls, and/or a compressing of the materials through a nip between a pair of heated calendering rollers, as well as various combinations of these methods.

Samples that were humidified were placed in a controlled humidity chamber at 80% Relative Humidity and 100° F. (38° C.) for 24–65 hours, then equilibrated at 50%±2% relative humidity, and 73.4° F.±1.8° F. (23° C.±1° C.). Resulting moisture pickup after equilibration is noted in TABLES 4 and 5.

Figure 7:
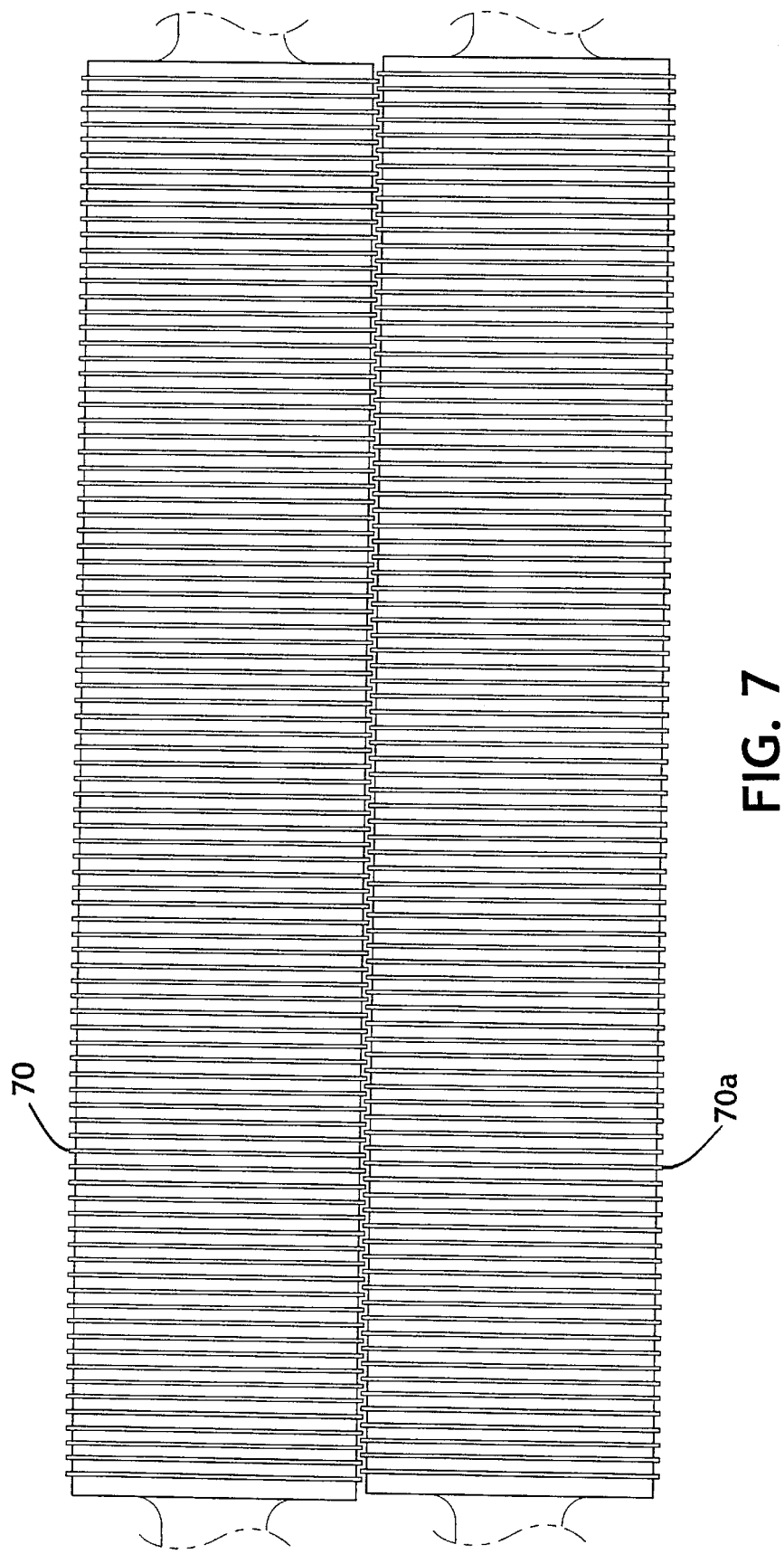
FIG. 7 representatively shows a cooperating pair of softening rollers employed to produce the absorbent body of the invention.

The mechanical softening of the materials was achieved with a set of matched grooved rolls 70 and 70a. As representatively shown in FIGS. 7 and 8, each of the counter-rotating grooved rollers 70 and 70a includes an alternating series of cooperating peaks 72 and lands 76. The width 78 of the peak is 0.031 inch (0.79 mm), the width 80 of the land is 0.094 inch (2.39 mm). The height 82 of the peak (or equivalently, the depth of the land) is 0.09 inch (2.29 mm). The center-to-center distance 84 between adjacent peaks that are on the same roller is 0.125 inch (3.18 mm). The peaks of one roll are substantially centered in the lands of the other, matched roll. The "engagement" distance 90 between the rollers 70 and 70a is measured as the distance from the peak provided by the first roll to the adjacently positioned peak provided by the second roll when the peaks of one roll penetrate into the grooves of the matched roll. A "gap" is measured when the peaks of one roller do not penetrate into the grooves of the second roller. The amount of engagement between the grooves of the softening rolls is indicated in TABLES 2 an 5.

Examples of suitable circumferentially-grooved rollers are described in U.S. Pat. No. 4,921,643 entitled WEB PROCESSING WITH TWO MATED ROLLS by R. Walton et al., which issued May 1, 1990. The retarding fingers described in the U.S. Pat. No. 4,921,543 were not employed in the softening of the examples presented herein. Methods for softening a wet-formed, superabsorbent-containing web are described in U.S. patent application Ser. No. 09/334,186 entitled PROCESS FOR COMPRESSING A WEB WHICH CONTAINS SUPERABSORBENT MATERIAL by S. K. Melius et al., which was filed Jun. 16, 1999. The entire disclosures of these documents are incorporated herein by reference in a manner that is consistent herewith.

A compressing and densification of the materials was accomplished using a pair of induction heated, calendering rolls of 9.5 inch (24.13 cm) diameter, at a speed of 50 ft/min (15.24 m/min), at a temperature of 220–225° F. (104–107° C.), and with the gap between the rolls set as specified in TABLES 3 and 5. The samples were between 6 and 7 inches (15.2 cm–17.9 cm) in width along the axial length of the rolls. The pressure applied to the rolls and the weight of the rolls themselves resulted in a force of 4380 lb (1987 kg) on the samples. The resulting gap when the sample was passed through the calendar was not measured. It would be equivalent to or larger than the gap that was set prior to calendering. If the pressure provided by the rolls was insufficient to prevent the rolls from lifting off their associated gap stops, the resulting gap would be larger. Suitable calendering rolls are available from Tokuden Co. a company having offices in Kyoto, Japan; or Tokuden, Inc. a company having offices in Norcross, Ga.

Examples 1A through 16B:

The superabsorbent (SAP) used for all of the Examples was FAVOR SXM 880 superabsorbent available from Stockhausen, Inc. Where a KYMENE binder was employed, the binder was KYMENE 557LX available from Hercules, Inc. of Wilmington, Del. The KYMENE binder was used in the amount of 10 pounds of KYMENE binder solids per 1 metric ton of furnish for all Examples; except for Examples 13A, 13B, 13C. and 13D, in which the KYMENE binder was not added. A BEROCEL 596 debonding agent, available from Eka Chemicals, a business having offices located at Marietta, Ga., was used in Example 4A only. The BEROCEL debonding agent was added to the mixture before agitation by employing an air stream blown into the forming chamber.

Examples 1A through 6A were made according to the above-described procedure using room temperature water. Examples 7A through 15A were made according to the above procedure using ice water to slow the swelling of the superabsorbent. Example 16A is an example of a wet-formed material produced with the foamed fiber slurry process.

TABLE 1 shows the composition and resulting Edge-wise Compression value, Modified Circular Bend value and density of the listed examples. Examples 1A and 4A are examples that would be useful in the present invention. The other examples are given for the purposes of comparison to the modified materials, as described in TABLES 2, 3, 4, and 5.

TABLE I

| Example | SAP % | NHB416 % | CR0054 % | Eucalyptus % | EC Value (g/gsm) | MCB Value (g/gsm) | DENSITY (g/cc) |
|---|---|---|---|---|---|---|---|
| 1A | 60 | 22 | 18 | 0 | 5.97 | 0.59 | 0.08 |
| 2A | 40 | 33 | 27 | 0 | 11.1 | 0.88 | 0.07 |
| 3A | 25 | 41.25 | 33.75 | 0 | 19.05 | 1.26 | 0.07 |
| 4A | 24 | 22.8 | 53.2 | 0 | 7.06 | 0.42 | 0.05 |
| 5A | 24 | 22.8 | 53.2 | 0 | 12.64 | 0.54 | 0.07 |
| 6A | 15 | 46.75 | 38.25 | 0 | 25.75 | 1.15 | 0.06 |
| 7A | 60 | 18 | 22 | 0 | 11.14 | 0.84 | 0.09 |
| 8A | 60 | 22 | 18 | 0 | 19.14 | 1.79 | 0.1 |
| 9A | 40 | 60 | 0 | 0 | 12.27 | 1.14 | 0.07 |
| 10A | 40 | 36 | 24 | 0 | 26.44 | 2 | 0.09 |
| 11A | 40 | 27 | 33 | 0 | 25.15 | 2.1 | 0.08 |
| 12A | 40 | 0 | 60 | 0 | 34.88 | 2.05 | 0.09 |
| 13A | 40 | 0 | 60 | 0 | 21.86 | 0.54 | 0.08 |
| 14A | 40 | 0 | 0 | 60 | 18.92 | 1.23 | 0.09 |
| 15A | 40 | 0 | 30 | 30 | 32.13 | 1.98 | 0.12 |
| 16A | 25 | 22.5 | 52.5 | 0 | 4.52 | 0.28 | 0.05 |

TABLE 2 shows the effect of softening of the materials with matched grooved rolls: The unsoftened material (designated with a suffix "A") is shown for comparison to the softened material (designated with a suffix "B", "C" or "D"). Example 1D and 14C are comparative examples showing that too much mechanical softening of the web can hurt the wet integrity of the material.

TABLE 2

| Example | Softening Roll Engagement (mm) | # passes through Softening Roll | EC Value (g/gsm) | MCB Value (g/gsm) | DENSITY (g/cc) |
|---|---|---|---|---|---|
| 1A | — | — | 5.97 | 0.59 | 0.08 |
| 1B | 0.762 | 1 | 1.78 | 0.34 | 0.15 |
| 1C | 1.016 | 1 | 1.83 | 0.3 | 0.16 |
| 1D | 1.270 | 1 | 1.66 | 0.27 | 0.16 |
| 2A | — | — | 11.1 | 0.86 | 0.07 |
| 2B | 1.270 | 1 | 3.39 | 0.76 | 0.14 |
| 2C | 1.778 | 1 | 3.68 | 0.65 | 0.15 |
| 7A | — | — | 11.14 | 0.84 | 0.09 |
| 7B | 1.270 | 1 | 3.41 | 0.66 | 0.18 |
| 8A | — | — | 19.14 | 1.79 | 0.1 |
| 8B | 1.270 | 1 | 7.07 | 1.13 | 0.16 |
| 9A | — | — | 12.27 | 1.14 | 0.07 |
| 9B | 1.270 | 1 | 5.77 | 1.08 | 0.13 |
| 10A | — | — | 26.44 | 2 | 0.09 |
| 10B | 1.778 | 1 | 8.03 | 1.95 | 0.17 |
| 13A | — | — | 21.86 | 0.54 | 0.08 |
| 13B | 1.778 | 1 | 7.6 | 0.66 | 0.19 |
| 14A | — | — | 18.92 | 1.23 | 0.09 |
| 14B | 1.778 | 1 | 3.68 | 0.4 | 0.14 |
| 14C | 1.778 | 2 | 1.43 | 0.19 | 0.16 |

TABLE 3 shows the effect of softening by Heated Calendering. The unsoftened material (designated with the suffix "A") is shown for comparison to the softened material.

TABLE 3

| Example | Calender Gap (mm) | EC Value (g/gsm) | MCB Value (g/gsm) | DENSITY (g/cc) |
|---|---|---|---|---|
| 4A | — | 7.06 | 0.42 | 0.05 |
| 4B | 1.016 | 4.65 | 0.33 | 0.1 |
| 4C | 0.762 | 3.95 | 0.42 | 0.13 |
| 5A | — | 12.64 | 0.54 | 0.07 |
| 5B | 1.016 | 8.3 | 0.52 | 0.12 |
| 5C | 0.762 | 7.46 | 0.55 | 0.15 |
| 16A | — | 4.52 | 0.28 | 0.05 |

TABLE 3-continued

| Example | Calender Gap (mm) | EC Value (g/gsm) | MCB Value (g/gsm) | DENSITY (g/cc) |
|---|---|---|---|---|
| 16B | 0.762 | 2.27 | 0.35 | 0.15 |

TABLE 4 shows softening by humidification. The unsoftened material (having the suffix "A") is shown for comparison to the softened material.

TABLE 4

| Example | Moisture Pickup % | EC Value (g/gsm) | MCB Value (g/gsm) | DENSITY (g/cc) |
|---|---|---|---|---|
| 1A | — | 5.97 | 0.59 | 0.08 |
| 1E | 3 | 3.37 | 0.42 | 0.08 |

TABLE 5 shows softening by a combination of methods. The unsoftened material (designated with the suffix "A") is shown for comparison to the softened material. A dash in the table means that the softening process was not done on that example. Where samples were subjected to multiple softening steps, the steps were conducted in the order (from left to right) listed in the Table (e.g. humidified, softening rolls, heated calendar rolls).

TABLE 5

| Example | % Moisture Pickup | Softening Roll Engagement (mm) | # passes through Softening Roll | Calender Gap (mm) | EC Value (g/gsm) | MCB Value (g/gsm) | DENSITY (g/cc) |
|---|---|---|---|---|---|---|---|
| 1A | — | — | — | — | 5.97 | 0.59 | 0.08 |
| 1F | 3 | 0.762 | 1 | — | 2.51 | 0.42 | 0.17 |
| 1G | 3 | 1.016 | 1 | — | 1.4 | 0.38 | 0.18 |
| 1H | 5 | — | — | 0.762 | 2.99 | 0.48 | 0.26 |
| 1I | 5 | — | — | 1.016 | 2.26 | 0.52 | 0.26 |
| 2A | — | — | — | — | 11.1 | 0.86 | 0.07 |
| 2D | 5 | 0.762 | 1 | — | 5.82 | 0.81 | 0.15 |
| 2E | 5 | 1.270 | 1 | — | 5.94 | 0.69 | 0.17 |
| 2F | 5 | — | — | 1.270 | 4.64 | 0.74 | 0.19 |
| 3A | — | — | — | — | 19.05 | 1.26 | 0.07 |
| 3B | 11 | 0.762 | 2 | — | 5.34 | 1 | 0.17 |
| 3C | 11 | 1.778 | 2 | — | 4.37 | 0.82 | 0.19 |
| 4A | — | — | — | — | 7.06 | 0.42 | 0.05 |
| 4D | 0.3 | — | — | 1.016 | 2.21 | 0.4 | 0.11 |
| 4E | 0.3 | — | — | 0.762 | 2.36 | 0.36 | 0.16 |
| 5A | — | — | — | — | 12.64 | 0.54 | 0.07 |
| 5D | 1 | — | — | 1.016 | 4.15 | 0.52 | 0.13 |
| 5E | 1 | — | — | 0.762 | 4.54 | 0.58 | 0.16 |
| 6A | — | — | — | — | 25.75 | 1.15 | 0.06 |
| 6B | 9 | 0.762 | 2 | — | 8.12 | 0.86 | 0.17 |
| 6C | 9 | 1.778 | 2 | — | 5.53 | 0.84 | 0.18 |
| 7A | — | — | — | — | 11.14 | 0.84 | 0.09 |
| 7C | 18 | 1.270 | 1 | — | 3.02 | 0.79 | 0.19 |
| 8A | — | — | — | — | 19.14 | 1.79 | 0.1 |
| 8C | 18 | 1.270 | 1 | — | 5.5 | 0.95 | 0.2 |
| 9A | — | — | — | — | 12.27 | 1.14 | 0.07 |
| 9C | 6 | 1.270 | 1 | — | 3.66 | 0.74 | 0.18 |
| 9D | 6 | 1.270 | 1 | 1.270 | 3.69 | 0.63 | 0.19 |
| 10A | — | — | — | — | 26.44 | 2 | 0.09 |
| 10C | 10 | 1.778 | 1 | — | 6.79 | 1.37 | 0.18 |
| 11A | — | — | — | — | 25.15 | 2.1 | 0.08 |
| 11B | 14 | 1.778 | 1 | — | 6.85 | 1.38 | 0.19 |
| 12A | — | — | — | — | 34.88 | 2.05 | 0.09 |
| 12B | 7 | 1.778 | 1 | — | 8.5 | 2.34 | 0.21 |
| 13A | — | — | — | — | 21.86 | 0.54 | 0.08 |
| 13C | 6 | 1.778 | 1 | — | 6.19 | 0.81 | 0.22 |
| 13D | 6 | 1.778 | 1 | 1.270 | 6.26 | 0.75 | 0.23 |
| 14A | — | — | — | — | 18.92 | 1.23 | 0.09 |
| 14D | 7 | 1.778 | 1 | — | 5.18 | 0.5 | 0.17 |
| 14E | 7 | 1.016 | 2 | — | 2.69 | 0.3 | 0.16 |
| 15A | — | — | — | — | 32.13 | 1.98 | 0.12 |
| 15B | 6 | 1.270 | 2 | — | 6.75 | 0.91 | 0.19 |
| 15C | 6 | 1.778 | 2 | — | 5.41 | 1.3 | 0.2 |

The diaper constructions described in the following Examples 17 through 22 include a waterproof, polyethylene film backsheet layer, a liquid pervious 0.5 osy (17 g/m$^2$) spunbonded polypropylene bodyside liner which provided the appointed topsheet layer, an absorbent core sandwiched between the backsheet and topsheet layers, and a 80 gsm bonded-carded-web surge management material positioned between the topsheet and the absorbent core. The surge management material is composed of a mixture of 40% by weight of 6 denier polyester fibers from Hoechst Celanese, and 60% by weight of 3 denier, polyethylene-polypropylene sheath-core crimped fibers available from Chisso Corporation of Japan. Each diaper also has a fastening mechanism and gasketing features. The diapers have different absorbent cores, as described in the following Examples. The absorbent core includes a wet-formed retention portion composed of the material identified in the specific Examples described below. Each absorbent core has a surface area of about 370 cm$^2$, with a crotch width at the narrowest point of the absorbent core being about 2.5 inches (about 6.3 cm), and a longest dimension of the absorbent core being about 15 inches (about 38 cm). When an upper and lower absorbent layer are combined to form the absorbent core (as representatively shown in FIGS. 3, 5 and 6), the upper layer is a rectangle measuring 2.5 inches (6.3 cm) wide in the cross-direction 24 and 8 inches (20.3) long in the longitudinal direction 26. The upper layer is arranged to provide the absorbent layer which is relatively closer to the wearer's body, and is placed adjacent the lower layer at a location starting 1 inch (2.54 cm) from the appointed front waistband edge of the lower layer, full-area pad.

Example 17

The diaper of this example includes an absorbent core having a single layer of the wet-laid, superabsorbent-containing absorbent of the material described in Example G1. The absorbent material has a basis weight of 500 gsm, an EC value of 1.4 g/gsm, a MCB value of 0.38 g/gsm, and a density of 0.18 g/cm$^3$.

Example 18

The diaper of this example includes an absorbent core having a single layer of the wet-laid, superabsorbent-containing absorbent of the material described in Example 2B. The wet-laid absorbent has a basis weight of 600 gsm, an EC value of 3.39 g/gsm, a MCB value of 0.76 g/gsm, and a density of 0.14 g/cm$^3$.

Example 19

The diaper of this example includes an absorbent core having a layer of airlaid mixture of superabsorbent and fluff located on top of a layer of the material described in Example 14E. The airlaid mixture of superabsorbent and fluff has a basis weight of 300 gsm and a density of 0.15 g/cm$^3$. The airlaid mixture comprises 30% superabsorbent, 65% woodpulp fluff, and 5% binder fiber. The wet-formed material of Example 14E has a basis weight of 400 gsm, an EC value of 2.69 g/gsm, a MCB value of 0.3 g/gsm, and a density of 0.16 g/cm$^3$.

Example 20

The diaper of this example includes an absorbent core having an upper, bodyside layer of the material described in Example 4D, and a lower layer of airlaid superabsorbent and fluff. The material of Example 4D has a basis weight of 400 gsm, an EC value of 2.21 g/gsm, a MCB value of 0.4 g/gsm, and a density of 0.11 g/cm$^3$. The airlaid superabsorbent and fluff has a basis weight of 400 gsm and is composed of 40% SAP and 60% woodpulp fluff at a density of 0.2 g/cm$^3$.

Example 21

The diaper of this example includes an absorbent core having an upper, bodyside layer and a lower, outward side layer. The upper layer is composed of the material of Example 4D, and has a basis weight of 400 gsm, an EC value of 2.21 g/gsm, a MCB value of 0.4 g/gsm, and a density of 0.11 g/cm$^3$. The lower layer is composed of the material of Example 14E, and has a basis weight of 400 gsm, an EC value of 2.69 g/gsm, a MCB value of 0.3 g/gsm, and a density of 0.16 g/cm$^3$.

Example 22

The diaper of this example includes an absorbent core having an upper layer and a lower layer. The upper layer is composed of the material of Example 4D, and has a basis weight of 400 gsm, an EC value of 2.21 g/gsm, a MCB value of 0.4 g/gsm, and a density of 0.11 g/cm$^3$. The lower layer is composed of the material of Example 1G, and has a basis weight of 350 gsm, an EC value of 1.4 g/gsm, a MCB value of 0.38 g/gsm, and a density of 0.18 g/cm$^3$.

Example 23

An adult incontinence pad has a shaped, contoured chassis which includes a water proof polyethylene film baffle layer and liquid pervious 17 gsm spunbonded polypropylene bodyside liner, both of which are 276 mm long, 83 mm wide at their widest points and 80 mm wide in their center regions between their widest points. An absorbent core is sandwiched between the baffle layer and bodyside liner. In addition, a 38 mm wide by 178 mm long, 120 gsm bonded-carded-web surge management material is sandwiched between the liquid pervious bodyside liner and the absorbent core. The surge management material includes a mixture of 40% by weight 6 denier polyester fibers from Hoechst Celanese, and 60% by weight 3 denier sheath core polyethylene/polypropylene crimped fibers from Chisso Corporation of Japan. The absorbent core includes two layers of wet-laid, superabsorbent containing, absorbent material constructed in accordance with Example 11B at a basis weight of 316 gsm per layer and with a total surface area of 152 square centimeters. The absorbent core has a length of 254 mm, a width of 67 mm at the widest point and a width of 60 mm in the longitudinal center of the absorbent. The material is softened and densified through softening and calendering rolls to a density of 0.19 g/cm$^3$. The absorbent core has an EC value of 6.85 g/gsm and a MCB value of 1.38 g/gsm.

Example 24

An adult incontinence undergarment has a shaped chassis which includes a water proof polyethylene film backsheet and a liquid pervious 17 gsm spunbonded polypropylene bodyside liner both of which are 686 mm long, 218 mm wide at their widest points and 165 mm wide at the center regions between their widest points. An absorbent core is sandwiched between the backsheet and liner. In addition, a 65 mm wide by 325 mm long 85 gsm bonded carded wet surge management material is sandwiched between the liquid pervious bodyside liner and the absorbent core. The surge management material includes a mixture of 40% by weight 6 denier polyester fibers from Hoechst Celanese, and 60% by weight 3 denier sheath core polyethylene/polypropylene crimped fibers from Chisso Corporation of Japan. The absorbent core comprises two layers of a wet-laid, superabsorbent containing, absorbent material constructed in accordance with Example 11B. The absorbent core has a basis weight of 270 gsm per layer and a total surface area of 485 square centimeters. The absorbent material has a length of 432 mm, a width of 160 mm at its two longitudinal ends, and a width of 92 mm at a longitudinal center of the core. The absorbent core material is softened and densified through softening and calendering rolls to a density of 0.19 g/cm$^3$. The absorbent core has an EC value of 6.85 g/gsm and a MCB value of 1.38 g/gsm.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article having a longitudinal direction and a lateral cross-direction, said article comprising:
   a liquid permeable topsheet layer;
   a substantially liquid impermeable backsheet layer; and
   an absorbent retention portion sandwiched between said topsheet and backsheet layers,
      said retention portion including a wet-formed mixture of fibers and superabsorbent material, and
      said retention portion having an Edge-wise Compression value of not more than a maximum of about 6 g/gsm, and a Modified Circular Bend value of at least a minimum of about 0.3 g/gsm.

2. An article as recited in claim 1, wherein said retention portion has an Edge-wise Compression value of not more than about 3 g/gsm.

3. An article as recited in claim 1, wherein said retention portion has a Modified Circular Bend value of at least about 0.4 g/gsm.

4. An article as recited in claim 1, wherein said retention portion contains at least about 5 wt % of superabsorbent material.

5. An article as recited in claim 1, wherein said retention portion contains at least about 30 wt % of superabsorbent material.

6. An article as recited in claim 1, wherein said retention portion contains a separately provided binder material which is additional to said fibers and superabsorbent material, said binder material provided in an amount of not more than about 25 wt %, as determined with respect to a total weight of said retention portion.

7. An article as recited in claim 1, wherein said retention portion contains synthetic polymer fiber having a synthetic fiber length greater than about 2 mm, said synthetic fiber in an amount which is not more than about 50 wt % of a total amount of fibrous material in said retention portion.

8. An article as recited in claim 1, wherein said retention portion contains stiffened cellulose fibers.

9. An article as recited in claim 1, wherein said retention portion contains hydrophilic, crimped, synthetic fiber in an amount which is not more than about 50 wt % of a total amount of fibrous material in said retention portion.

10. An article as recited in claim 1, wherein said retention portion has a dry thickness of not more than about 3 cm.

11. An article as recited in claim 1, wherein said retention portion has a dry density of not more than about 0.6 g/cm$^3$.

12. An article as recited in claim 1, wherein said retention portion has a dry tensile strength value of at least about 0.7 N/cm, as determined along said longitudinal direction of the article.

13. An article as recited in claim 1, wherein said retention portion includes a supplemental layer containing a matrix of cellulosic fibers and not more than about 50 wt % of superabsorbent material.

14. An article as recited in claim 13, wherein said supplemental layer is positioned on an outward side of said retention portion.

15. An article as recited in claim 13, wherein said supplemental layer is positioned on a bodyside of said retention portion.

16. An article as recited in claim 1, wherein said retention portion includes a supplemental retention layer containing a matrix of cellulosic fibers and not more than about 80 wt % of superabsorbent material.

17. An article as recited in claim 1, wherein said article has a front waistband portion, a back waistband portion and an intermediate portion interconnecting said front and back waistband portions.

18. An article as recited in claim 1, wherein said article further comprises a surge management layer positioned adjacent an outward side of said topsheet layer.

* * * * *